(12) United States Patent
Sanda

(10) Patent No.: US 7,440,606 B2
(45) Date of Patent: Oct. 21, 2008

(54) DEFECT DETECTOR AND DEFECT DETECTION METHOD

(75) Inventor: Akio Sanda, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 813 days.

(21) Appl. No.: 10/940,845

(22) Filed: Sep. 15, 2004

(65) Prior Publication Data

US 2005/0056797 A1  Mar. 17, 2005

(30) Foreign Application Priority Data

Sep. 17, 2003  (JP)  ............................. 2003-324958

(51) Int. Cl.
  *G06K 9/00*  (2006.01)
(52) U.S. Cl. ....................... 382/141; 382/148; 382/149; 356/237.2; 250/559.45
(58) Field of Classification Search ................ 382/146, 382/133, 141, 147, 311, 151, 148, 145, 149, 382/217–219, 228, 274, 275; 356/394, 398, 356/431, 237.2, 237.5, 237.4; 348/65, E7.085, 348/126, 130, 128, 87, 120; 359/368, 211, 359/218; 250/492.22, 310, 306, 396 R, 398, 250/559.45, 559.39, 548; 438/16; 702/40, 702/82, 172, 179, 194
  See application file for complete search history.

(56) References Cited

U.S. PATENT DOCUMENTS

| | | | | | |
|---|---|---|---|---|---|
| 4,589,140 | A | * | 5/1986 | Bishop et al. | ................ 382/148 |
| 5,245,671 | A | * | 9/1993 | Kobayashi et al. | .......... 382/150 |
| 5,333,207 | A | * | 7/1994 | Rutenberg | ................... 382/133 |
| 5,663,569 | A | * | 9/1997 | Hayano | ................. 250/559.45 |
| 5,764,536 | A | * | 6/1998 | Yamamoto et al. | ............ 701/81 |
| 5,784,484 | A | * | 7/1998 | Umezawa | .................... 382/148 |
| 6,195,119 | B1 | * | 2/2001 | Dianna et al. | ................. 348/65 |
| 6,504,948 | B1 | * | 1/2003 | Schemmel et al. | .......... 382/149 |
| 6,895,109 | B1 | * | 5/2005 | Schemmel et al. | .......... 382/149 |
| 7,127,099 | B2 | * | 10/2006 | Noy | ........................... 382/149 |

FOREIGN PATENT DOCUMENTS

| | | |
|---|---|---|
| JP | 2001-189358 | 7/2001 |
| JP | 2001-356099 A | 12/2001 |
| JP | 2002-323458 | 11/2002 |
| JP | 2003-58138 A | 2/2003 |
| JP | 2003-218181 | 7/2003 |
| JP | 2003-247816 A | 9/2003 |
| JP | 2004-78690 | 3/2004 |

* cited by examiner

*Primary Examiner*—Sheela C Chawan
(74) *Attorney, Agent, or Firm*—McDermott Will & Emery LLP

(57) ABSTRACT

A control part of a defect detector is provided with a magnification operation part, an inspected image display part and a master image display part. The magnification operation part operates a display magnification α1 (display magnification data) for a defective area on the basis of defective information. An imaging part images inspected image data so that an imaging magnification β1 reaches the display magnification α1, and the inspected image display part displays the inspected image data on a detection monitor. The master image data display part operates a display magnification α2 for master image data to be substantially identical to the display magnification α1, and displays the master image data on the detection monitor at the display magnification α2. Thus, the efficiency in a defect detecting operation of an operator is improved.

15 Claims, 19 Drawing Sheets

F I G . 1 2
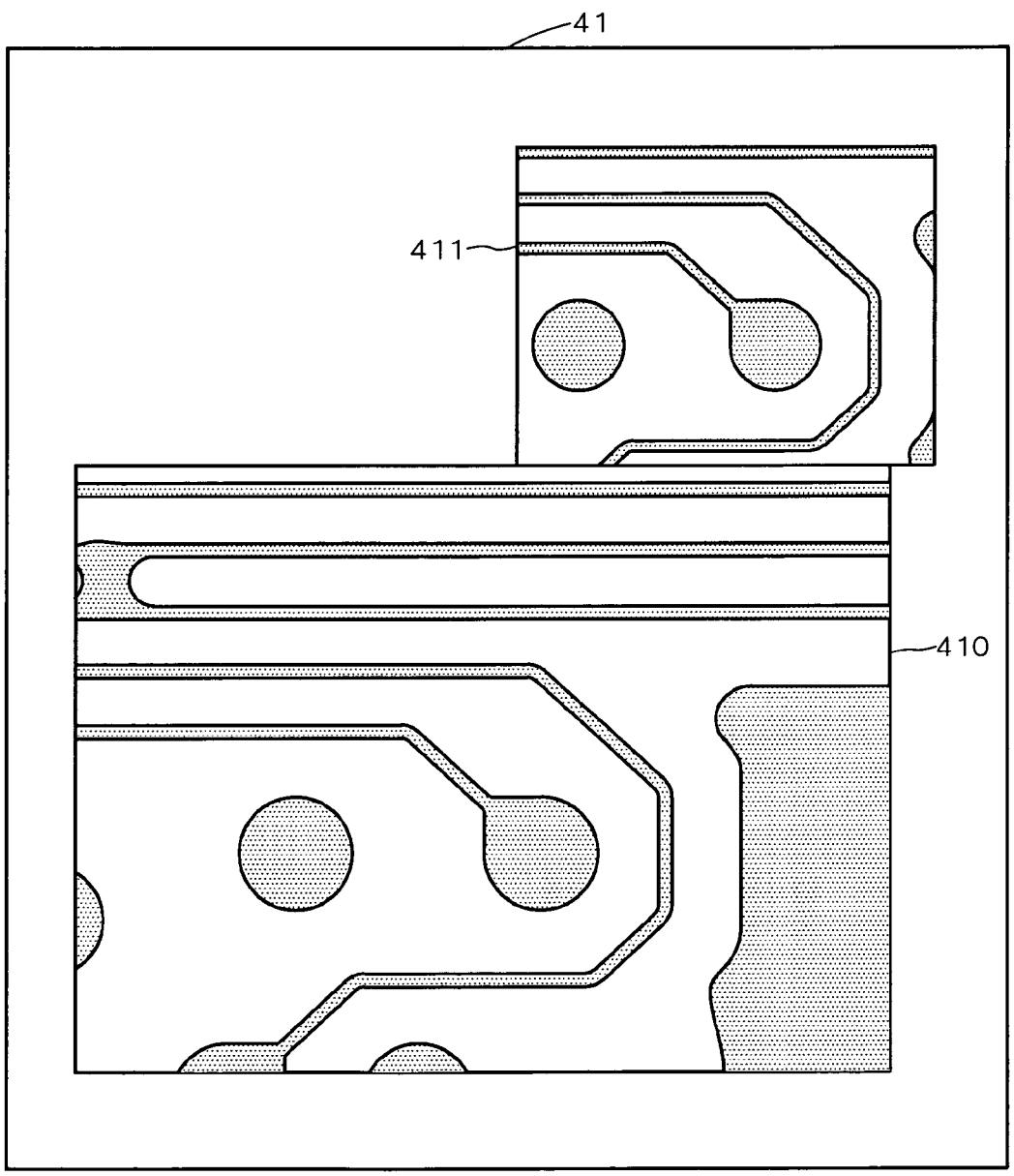

F I G . 1 6
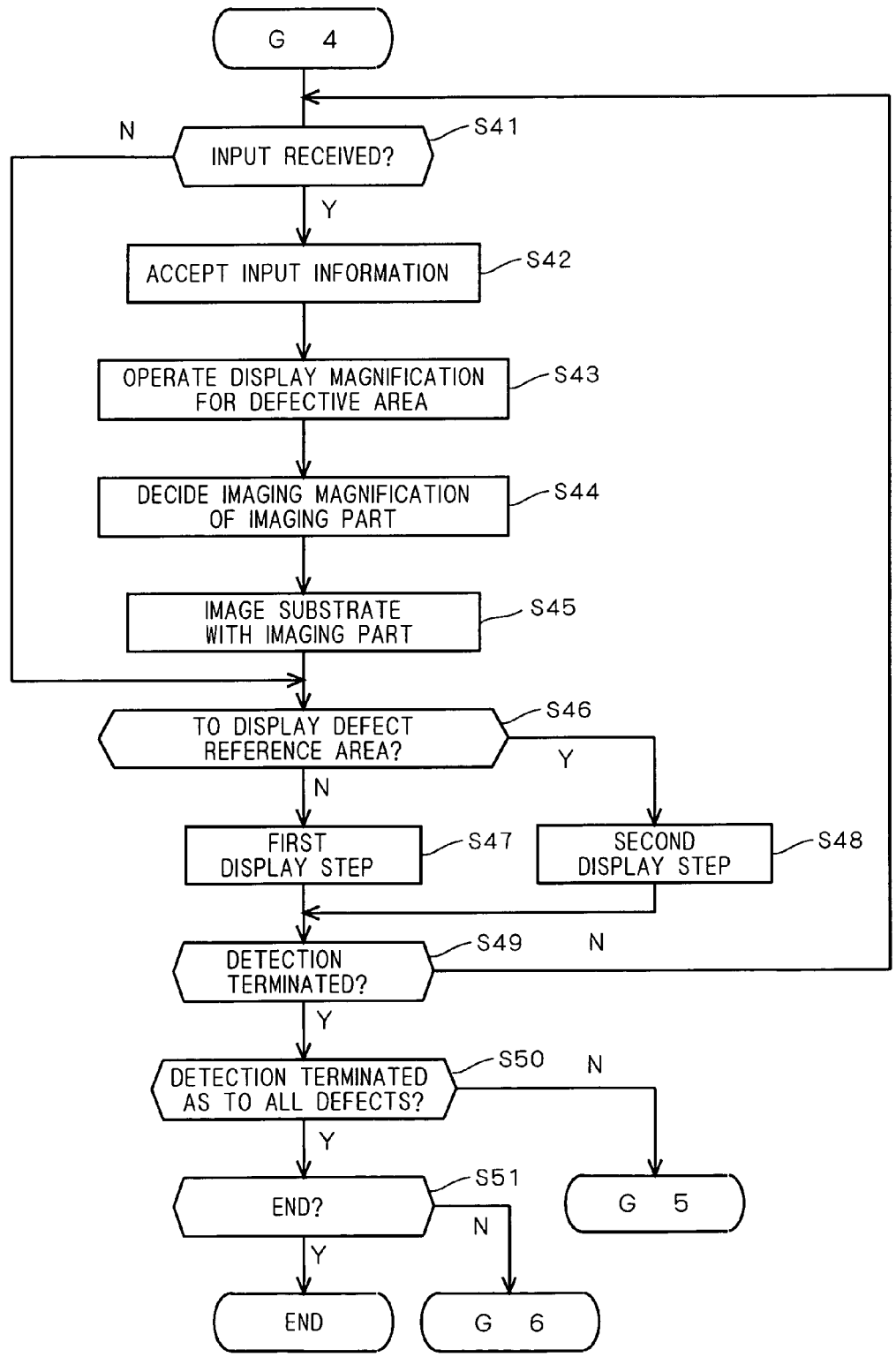

F I G. 1 8
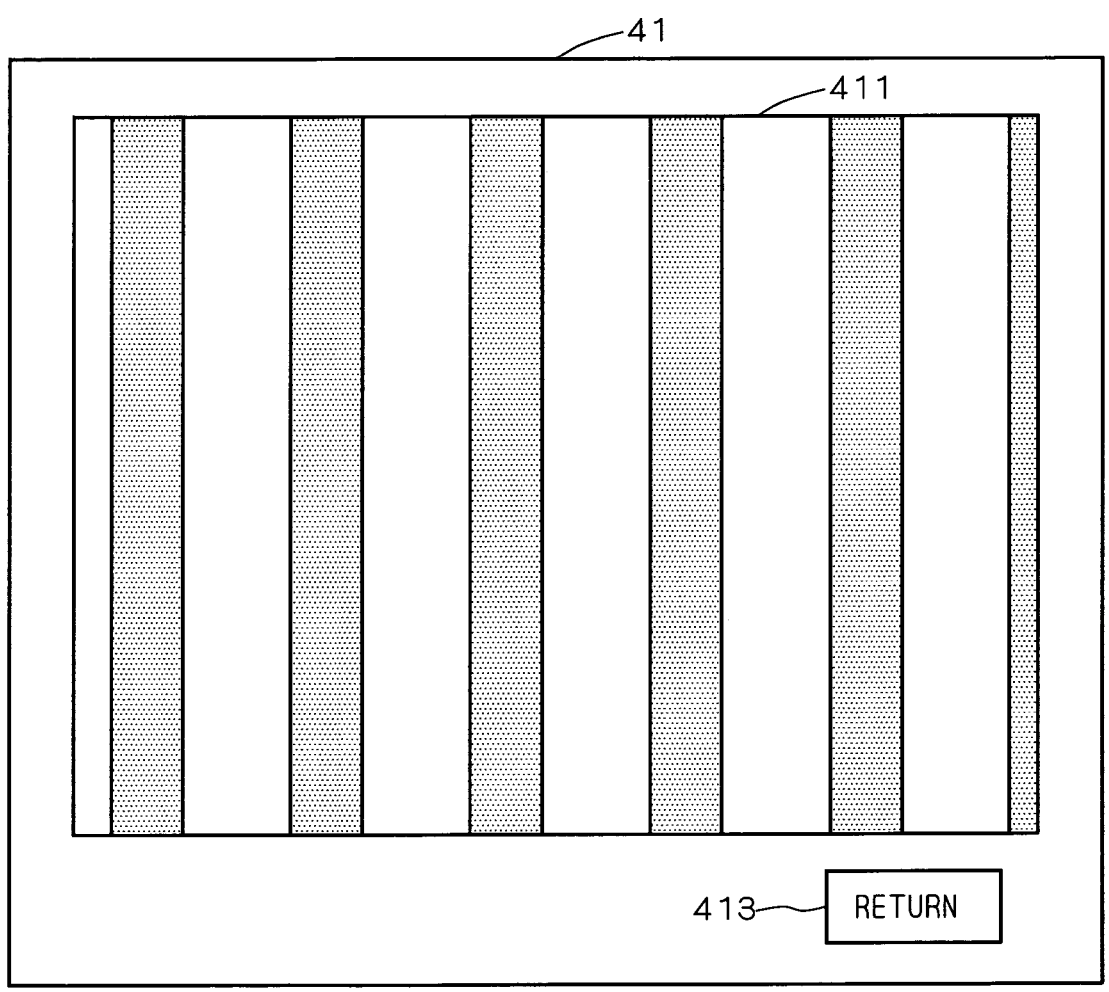

DEFECT DETECTOR AND DEFECT DETECTION METHOD

BACKGROUND OF THE INVENTION

1. Field of the Invention

The present invention relates to a technique of inspecting a pattern such as a wiring pattern formed on an inspected object such as a printed board or a film mask or a glass mask for preparing a printed board, and more particularly, it relates to a technique of displaying a reference image to be compared with an image of an inspected substrate.

2. Description of the Background Art

Generally proposed is a defect detector for detecting a defect in a wiring pattern or the like formed on the aforementioned inspected object (hereinafter referred to as "substrate"). This defect detector picks up an image (hereinafter referred to as "inspected image") of a defective portion (defective area) of the inspected substrate with an imager such as a CCD camera and displays the image on a monitor. The defect detector also displays an image (hereinafter referred to as "master image") of a reference master substrate similarly on the monitor. An operator of the conventional defect detector detects the defect of the inspected substrate on the basis of the inspected image with reference to the master image displayed in the aforementioned manner.

FIG. 21 illustrates an exemplary display of images on a display screen 100 of such a defect detector. Display areas 101 and 102 are set on the display screen 100 respectively. These display areas 101 and 102 display a master image and an inspected image respectively. As shown in FIG. 21, the conventional defect detector displays the reference master image and the inspected image respectively so that an operator can visually detect a defect. Further, the defect detector displays the inspected image at a display magnification identical to that for the master image, so that the operator can readily compare the two images with each other.

In an operation of detecting a defect of an inspected substrate, however, the operator may change the display magnification for the inspected image by operating an imager. In order to finely compare a circuit pattern of the inspected image with that of the master image, for example, the operator enlarges the inspected image displayed on the display area 102.

FIG. 22 illustrates the image (inspected image), displayed on the display area 102, enlarged by the operator. In this case, the conventional defect detector displays the master image and the inspected image at different display magnifications, and hence it is difficult to compare these images with each other and the working efficiency is disadvantageously reduced. Referring to FIG. 22, for example, the operator cannot determine whether a pattern 105 displayed on the display area 102 is to be compared with a pattern 103 or a pattern 104 displayed on the display area 101.

Also when the defect detector can change the display magnification for the master image, the operator must finely change the display magnification for the master image simultaneously with the operation of changing the display magnification for the inspected image, disadvantageously leading to reduction of the working efficiency.

SUMMARY OF THE INVENTION

The present invention relates to a technique of inspecting a pattern such as a wiring pattern formed on an inspected object such as a printed board or a film mask or a glass mask for preparing a printed board, and more particularly, the present invention is directed to a technique of displaying a reference image to be compared with an image of an inspected substrate.

Accordingly, a defect detector according to a preferred embodiment of the present invention comprises an image display system, a holding element holding an inspected object, an image acquisition element imaging the inspected object held by the holding element for acquiring inspected image data obtained by imaging a defective area of the inspected object having a defect, a first display control element displaying the inspected image data acquired by the image acquisition element on the image display system at a first display magnification and a second display control element displaying master image data to be compared with the defective area on the image display system at a second display magnification operated in response to the first display magnification.

Thus, the second display control element can display master image data imaged at an arbitrary imaging magnification in response to the first display magnification.

Preferably, the defect detector further comprises a size acquisition element acquiring information indicating the size of the defective area as to the inspected object held by the holding element and a display magnification operational element operating the first display magnification according to a prescribed algorithm on the basis of the information indicating the size of the defective area acquired by the size acquisition element.

Thus, the first display control element can automatically display the defective area at a proper magnification.

Preferably, the defect detector further comprises an operation part accepting input information from an operator, and the second display control element operates the second display magnification in response to the set first display magnification every time the first display magnification is set on the basis of the input information and displays the master image data on the image display system at the second display magnification.

Thus, it is possible to display the inspected image data at a display magnification desired by the operator and change the display magnification for the master image data following the display magnification for the inspected image data.

The present invention is also directed to a defect detecting method of defecting a defect on an inspected object, comprising a holding step of holding the inspected object, an image acquisition step of imaging the inspected object held in the holding step and acquiring inspected image data obtained by imaging a defective area of the inspected object having a defect, a first display step of displaying the inspected image data acquired in the image acquisition step on an image display system at a first display magnification and a second display step of displaying master image data to be compared with the defective area on the image display system at a second display magnification operated in response to the first display magnification.

Thus, it is possible to display master image data obtained at an arbitrary imaging magnification in response to the first display magnification.

Accordingly, an object of the present invention is to improve the working efficiency for an operation of detecting a defect.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 11 and 12 illustrate exemplary images displayed during a detective operation in the defect detector according to the first preferred embodiment;

FIGS. 15 and 16 are flow charts showing operations of the defect detector according to the second preferred embodiment;

FIG. 18 illustrates an exemplary display of master image data in the defect detector according to the second preferred embodiment;

DESCRIPTION OF THE PREFERRED EMBODIMENTS

Figure 1:
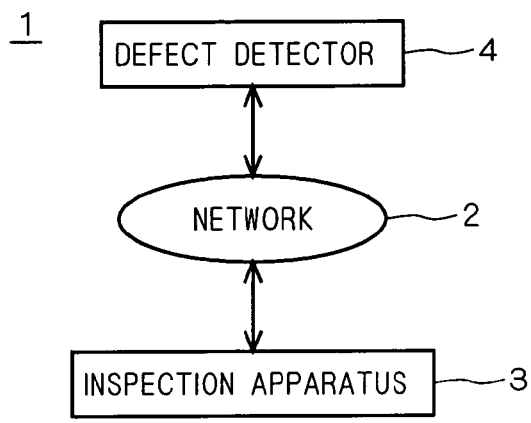
FIG. 1 illustrates the structure of a defect detection system including a defect detector according to a first preferred embodiment of the present invention.

FIG. 1 illustrates an exemplary structure of a defect detection system 1 including a defect detector 4 according to a first preferred embodiment of the present invention. In the structure of the defect detection system 1, an inspection apparatus 3 and the defect detector 4 are connected with each other through a network 2. The network 2 can be formed by any network such as a LAN (local area network) or a public communication line so far as the same is capable of data communication between the inspection apparatus 3 and the defect detector 4 through a prescribed communication protocol. Further, a plurality of inspection apparatuses 3 and a plurality of defect detectors 4 may be connected to the network 2.

Figure 2:
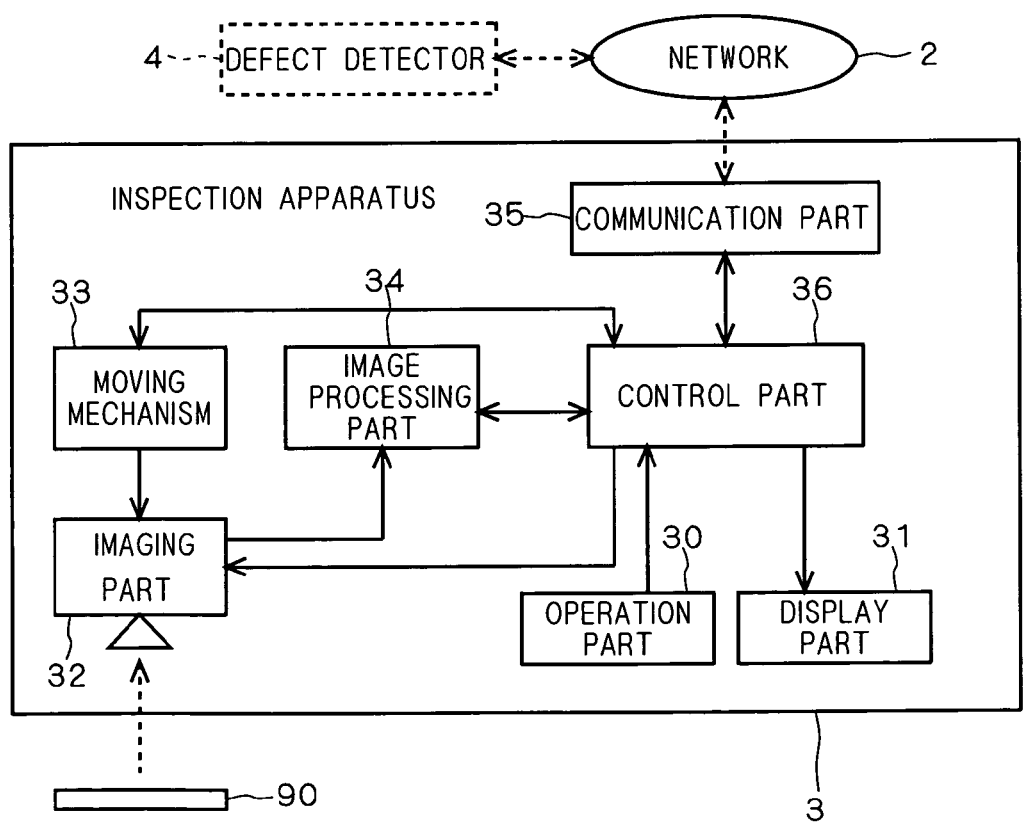
FIG. 2 is a block diagram showing the structure of an inspection apparatus.

FIG. 2 is a block diagram showing the structure of the inspection apparatus 3. The inspection apparatus 3 comprises an operation part 30 for inputting instructions of an operator, a display part 31 displaying operation information for the inspection apparatus 3, an imaging part 32 imaging an inspected surface of a substrate 90 to be inspected, a moving mechanism 33 moving the imaging part 32 to a prescribed position, an image processing part 34 processing image data obtained by the imaging part 32, a communication part 35 making data communication between the inspection apparatus 3 and the defect detector 4 through the network 2 and a control part 36.

The operator operates the operation part 30 for inputting an instruction in the inspection apparatus 3. More specifically, the operation part 30, formed by various buttons, a keyboard, a mouse and the like, may alternatively be formed by a trackball, a joystick or a touch panel. The display part 31, formed by a liquid crystal display displaying various data, may alternatively be formed by an LED (light-emitting diode) or a display lamp.

The imaging part 32, having a function equivalent to that of a general CCD camera, images the inspected surface of the substrate 90 as image data every block of a prescribed size and transmits the obtained image data to the image processing part 34.

The moving mechanism 33 moves the imaging part 32 to the prescribed position on the basis of a control signal from the control part 36. The moving mechanism 32 further detects the position of the imaging part 32 through a sensor such as an encoder and transmits the same to the control part 36.

The image processing part 34 performs prescribed image recognition processing on the image data obtained by the imaging part 32 (image data of each block of the substrate 90) and determines whether or not the substrate 90 has a defect.

The image processing part 34 further forms defective information 400 (FIG. 6) on the basis of the position of a detected defective area and the size of the defective area and transmits the same to the control part 36. The inspection apparatus 3 according to the first preferred embodiment employs the central coordinates of image data showing the defective area of the substrate 90 and the defective area of the image data as positional information of the defective area while employing the longitudinal and transverse dimensions of the defective area as size information thereof. However, the positional information and the size information of the defective area are not restricted to these. The inspection apparatus 3 may alternatively directly employ the coordinates of the substrate 90 as information indicating the position of the defective area, or may employ a pixel number as information indicating the size of the defective area, for example.

The communication part 35 has a function of acquiring the defective information 400 formed by the image processing part 34 through the control part 36 and transmitting the same to the defect detector 4 through the network 2. The control part 36, constituted of a CPU (not shown) and a memory (not shown), stores or operates various data and generates the control signal thereby controlling the remaining structures of the inspection apparatus 3.

Figure 3:
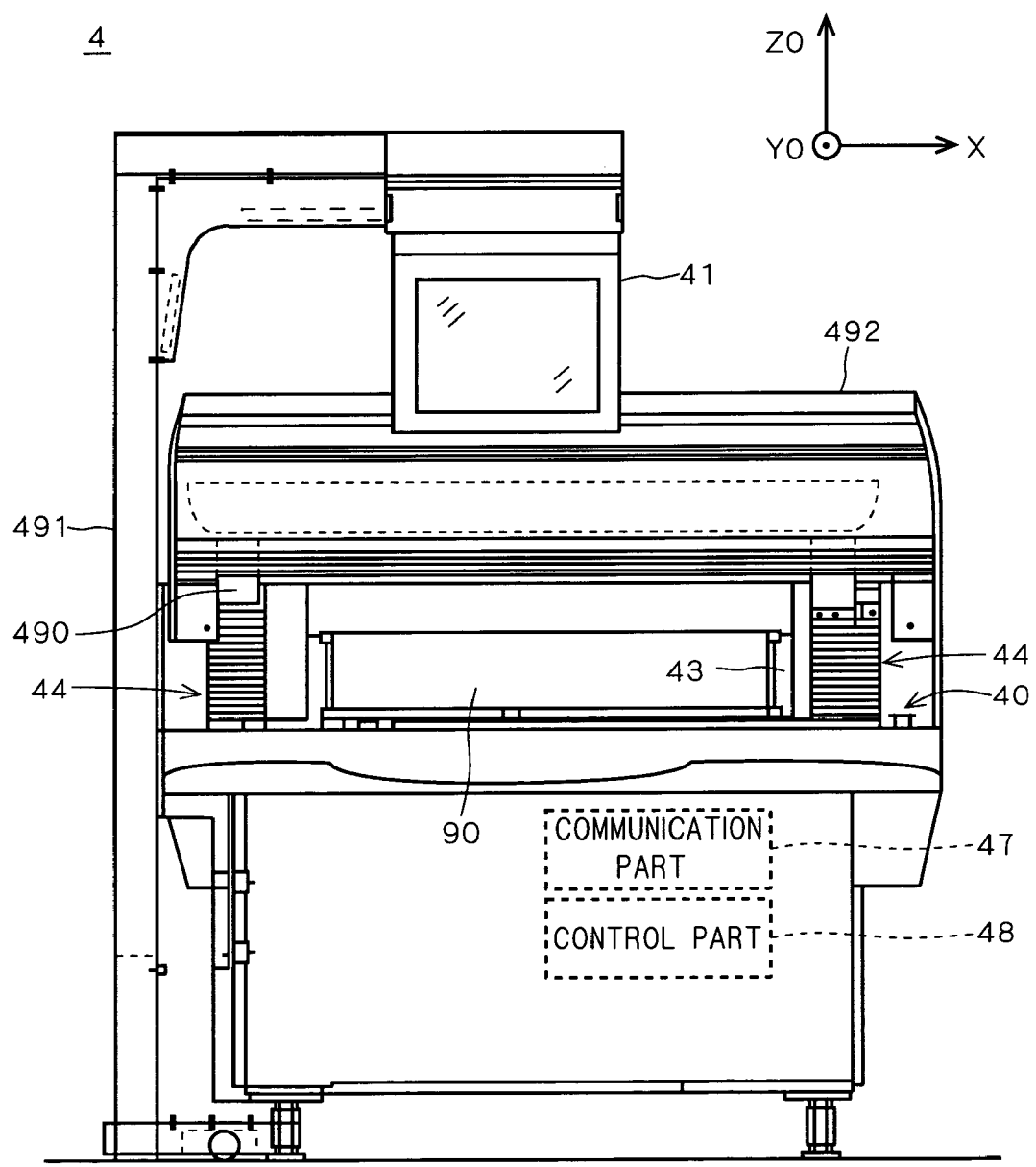
FIG. 3 is a front elevational view of the defect detector according to the first embodiment.
Figure 4:
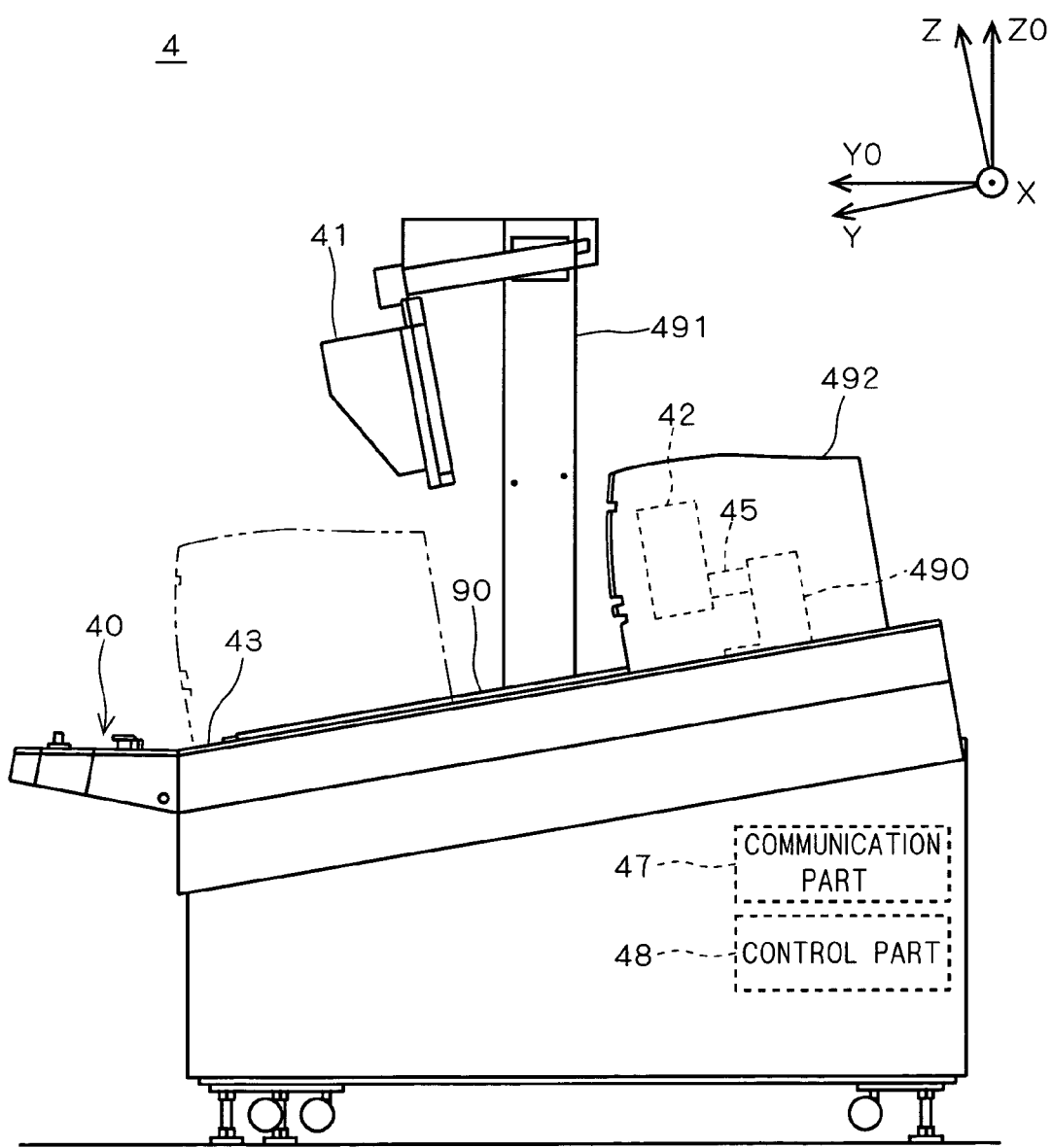
FIG. 4 is a side elevational view of the defect detector.
Figure 5:
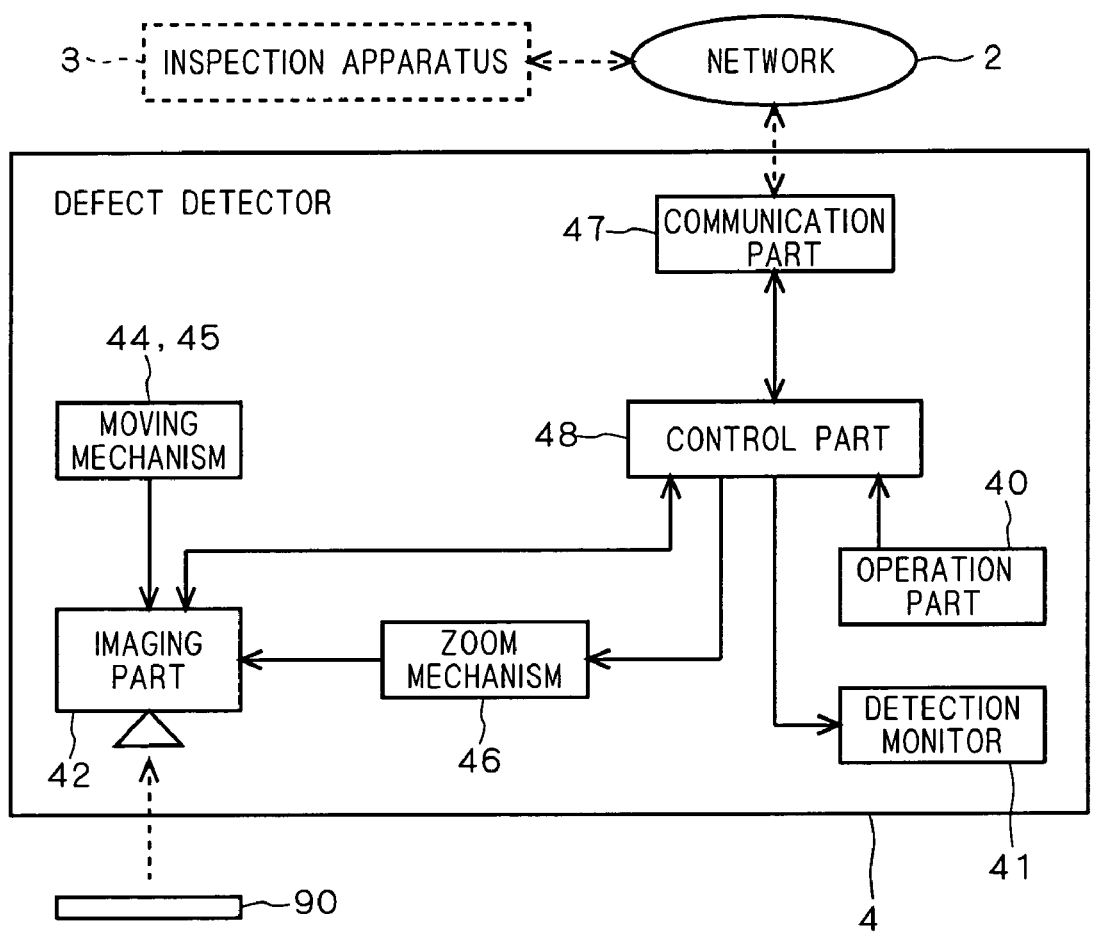
FIG. 5 is a block diagram showing the structure of the defect detector.

FIGS. 3 and 4 are a front elevational view and a side elevational view of the defect detector 4 respectively. FIG. 5 is a block diagram showing the structure of the defect detector 4. FIG. 3 defines a horizontal X0-axis, a Y-axis and a vertical Z0-axis, while FIG. 4 defines (1) an X-axis slightly downwardly inclined from the horizontal X0-axis in a vertical plane to be perpendicular to the Y-axis and (2) a Z-axis perpendicular to the X-axis and the Y-axis. The X-axis and the Z-axis, inclined from the X0-axis and the Z0-axis respectively in the first preferred embodiment, may alternatively coincide with the X0-axis and the Z0-axis respectively.

The defect detector 4 comprises an operation part 40 for inputting instructions of an operator, a detection monitor 41 displaying information and image data necessary for operating the defect detector 4 on a screen, an imaging part 42 imaging a defective portion of the substrate 90 as image data, an inspection stage 43 holding the substrate 90, a horizontal pair of moving mechanisms 44 arranged on both sides of the inspection stage 43 respectively, a moving mechanism 45 moving the imaging part 42 along the Y-axis direction, a zoom mechanism 46, a communication part 47 and a control part 48. The defect detector 4 also comprises a support table 490 having a bridging structure substantially horizontally extending between both side portions of the inspection stage 43, a support member 491 supporting the detection monitor 41 on the defect detector 4 and a protective cover 492 for protecting the imaging part 42.

In the defect detection system 1 making inspection by comparing the image data obtained by imaging the inspected substrate 90 with a master image (image data obtained by imaging a reference master substrate or digital bit-mapped image data created from CAD data, for example), the operator utilizes the defect detector 4 as an apparatus for visually detecting the defective portion, as described later in detail.

The operation part 40, formed by various buttons, a keyboard, a mouse and the like, may alternatively be formed by a trackball, a joystick or a touch panel. The operator may flip a dial or the like for directly driving an optical system of the imaging part 42 thereby operating the imaging magnification thereof. In this case, the dial or the like mounted on the zoom mechanism 46 corresponds to the operation part 40. In other words, the operation part 40 may be formed by any mechanism so far as the same is operated by the operator for inputting an instruction or the like in the defect detector 4.

The detection monitor 41 supported by the support member 491 on the defect detector 4 displays various data on its screen on the basis of a control signal from the control part 48. A liquid crystal display or the like, for example, corresponds to the detection monitor 41. The defect detector 4 according to the first preferred embodiment comprises a single detection monitor 41 mainly corresponding to the single display in the present invention.

The imaging part 42 is a general CCD camera photoelectrically converting light incident upon an optical axis (axis substantially perpendicular to the X-axis and the Y-axis) of the optical system such as an imaging lens through an image receiving element (CCD) provided therein thereby imaging the substrate 90 (inspected object) held on the inspection stage 43. The imaging part 42 transmits the obtained image data of the substrate 90 to the control part 48.

The upper surface of the inspection stage 43 is rendered substantially parallel to the X-Y plane, for hold the substrate 90 for inspection transferred to the defect detector 4 by the operator or a transfer mechanism (not shown) on a prescribed position.

The moving mechanisms 44 mounted on both sides of the support table 490 respectively move the support table 490 along the X-axis direction. Thus, the control part 48 can control the quantity of movement and the position of the support table 490. The moving mechanism 45 mounted on the support table 490 moves the imaging part 42 in the Y-axis direction along the support table 490. Thus, the control part 48 can control the quantity of movement and the position of the imaging part 42.

Well-known mechanisms employing servo motors, ball screws and feed nuts can be employed as the moving mechanisms 44 and 45 having the aforementioned functions, for example. The ball screws are extended along a prescribed direction and rotated by the servo motors for moving the feed nuts in the prescribed direction so that the control part 48 can control respective positions by controlling the rotational angles of the servo motors. The moving mechanisms 44 and 45 are not restricted to these but may alternatively be implemented by other well-known mechanisms, as a matter of course.

Thus, the defect detector 4 comprising the moving mechanisms 44 and 45 can move the imaging part 42 to an arbitrary position on the X-Y plane. Therefore, the imaging part 42 can image an arbitrary region (region having the defective area) of the substrate 90 held on the inspection stage 43.

The zoom mechanism 46 (not shown in FIGS. 3 and 4) has a function of deciding a zoom position of the optical system of the imaging part 42 on the basis of a control signal from the control part 48 thereby deciding the imaging magnification of the imaging part 42. The zoom mechanism 46 may be directly operable from the operation part 40.

The communication part 47 makes data communication between the defect detector 4 and the inspection apparatus 3 through the network 2. Thus, the defect detector 4 receives the defective information 400 transmitted from the inspection apparatus 3.

As shown in FIG. 5, the control part 48 is connected with the remaining structures of the defect detector 4 in a state capable of transferring signals. The control part 48 comprises a storage part 480 (FIG. 6) storing instructions from the operator, programs, various acquired data and the like for executing various operations through the CPU (not shown) and forming control signals thereby controlling the remaining structures of the defect detector 4 respectively.

Figure 6:
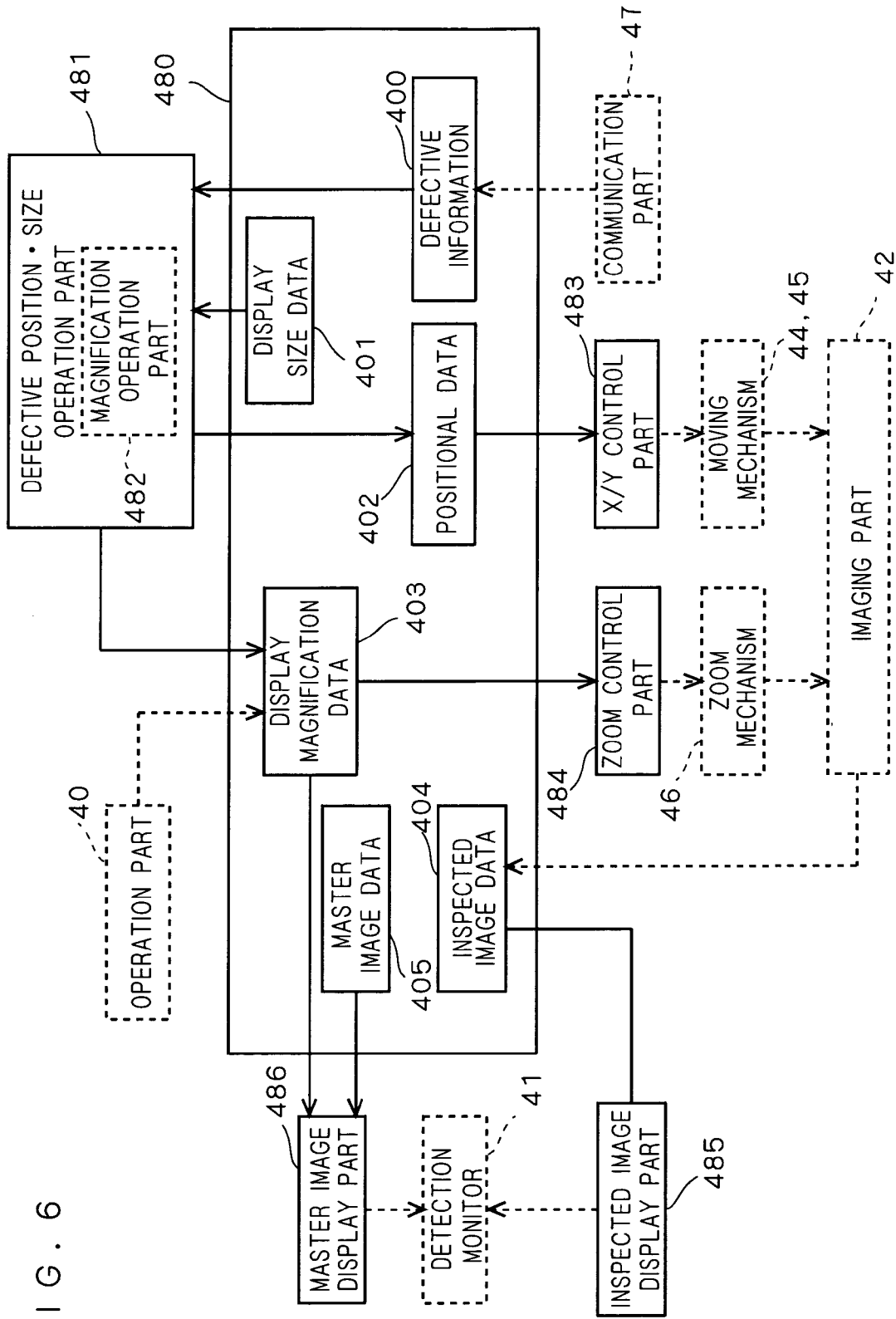
FIG. 6 is a block diagram showing the functional structure of a control part of the defect detector according to the first preferred embodiment along with data flows.

FIG. 6 is a block diagram showing the functional structure of the control part 48 along with signal flows. The CPU (not shown) of the control part 48 operates according to programs, thereby implementing a defective position-size operation part 481, a magnification operation part 482, an X/Y control part 483, a zoom control part 484, an inspected image display part 485 and a master image display part 486 in the functional structure shown in FIG. 6.

The defective position-size operation part 481 comprising the magnification operation part 482 generates positional data 402 indicating the position of the defective area on the substrate 90 held by the inspection stage 43 and display magnification data 403 indicating a display magnification $\alpha 1$ for the defective area.

In order to generate the positional data 402, the defective position-size operation part 481 refers to positional information of the defective area included in the defective information 400 received in the communication part 47 from the inspection apparatus 3 through the network 2. The positional data 402 includes the number of the block having the defective area (it is assumed that the surface of the substrate 90 is divided into blocks of a prescribed size and the position of each block is previously set in response to the number thereof) and the central position (X, Y) of the defective area in this block. Thus, the defect detector 4 can specify the position of the defective area on the substrate 90.

The defective position-size operation part 481 further acquires the size (Xf, Yf) of the defective area from the defective information 400 while acquiring a size (Xw, Yw) (hereinafter referred to as "defective area display size") for displaying the defective area on the detection monitor 41 from the display size data 401 and transfers the same to the magnification operation part 482. The defective position-size operation part 481 further generates the display magnification data 403 on the basis of an operational result of the magnification operation part 482.

The magnification operation part 482 operates the display magnification α1 for the defective area according to a prescribed algorithm based on the size of the defective area and the defective area display size and transfers the operational result to the defective position-size operation part 481. The initial value of the display size data 401 is previously set.

The X/Y control part 483 obtains the relative positions of the imaging part 42 and the defective area (substrate 90) on the basis of the positional data 402, generates a control signal (pulse signal) necessary for moving the imaging part 42 to a position for imaging the defective area and controls the moving mechanisms 44 and 45. More specifically, the Y/X control part 483 controls the moving mechanisms 44 on the basis of the number of the block and a value X and decides the position of the imaging part 42 in the X-axis direction. The X/Y control part 483 further controls the moving mechanism 45 on the basis of the number of the block and a value Y and decides the position of the imaging part 42 in the Y-axis direction.

The zoom control part 484 operates an imaging magnification β1 of the imaging part 42 for imaging the substrate 90 to be inspected according to a prescribed algorithm with reference to the display magnification data 403. The zoom control part 484 further obtains a quantity for driving the optical system of the imaging part 42 in response to the obtained imaging magnification β1 and controls the zoom mechanism 46 thereby deciding the imaging magnification β1 of the imaging part 42.

Thus, it follows that the defect detector 4 comprising the X/Y control part 483 and the zoom control part 484 decides the position of the imaged defective area and the imaging magnification therefor in response to the defective information 400 when the imaging part 42 images the defective area. Therefore, the defect detector 4 can acquire the inspected image data 404 of the defective area in response to the defective information 400 acquired by the communication part 47.

The inspected image display part 485 performs necessary image processing on the inspected image data 404 and thereafter displays this inspected image data 404 on the detection monitor 41.

The master image display part 486 operates a display magnification α2 for the master image data 405 to be compared with the defective area on the basis of the display magnification data 403, adjusts an enlargement ratio γ2 for the master image data 405 in response to the obtained display magnification α2 and displays the same on the detection monitor 41. In other words, the master image display part 486 mainly corresponds to the second display control element in the present invention. It is assumed that the master image data 405 obtained by imaging the overall area of a reference substrate with a prescribed imaging magnification β2 is previously acquired and preserved in the storage part 480 of the control part 48. The master image data 405 is preferably digital bit-mapped image data, and more preferably binarized bit-mapped image data. The master image display part 486 refers to the positional data 402 thereby deciding a displayed part (not shown) of the master image data 405.

Referring again to FIG. 5, the support table 490 has the bridging structure substantially horizontally extending between both sides of the inspection stage 43 along the Y-axis direction, for supporting the imaging part 42 on the inspection stage 43. The support table 490 is provided with the aforementioned moving mechanism 45.

The protective cover 492 not only protects the imaging part 42 but also prevents external incident light so that the imaging part 42 can clearly image the substrate 90. The protective cover 492 fixed to the support table 490 is moved by the moving mechanisms 44 in the X-axis direction along with the support table 490, for regularly covering the upper portion of the imaging part 42.

The defect detection system 1 has the aforementioned structure and functions.

Figure 7:
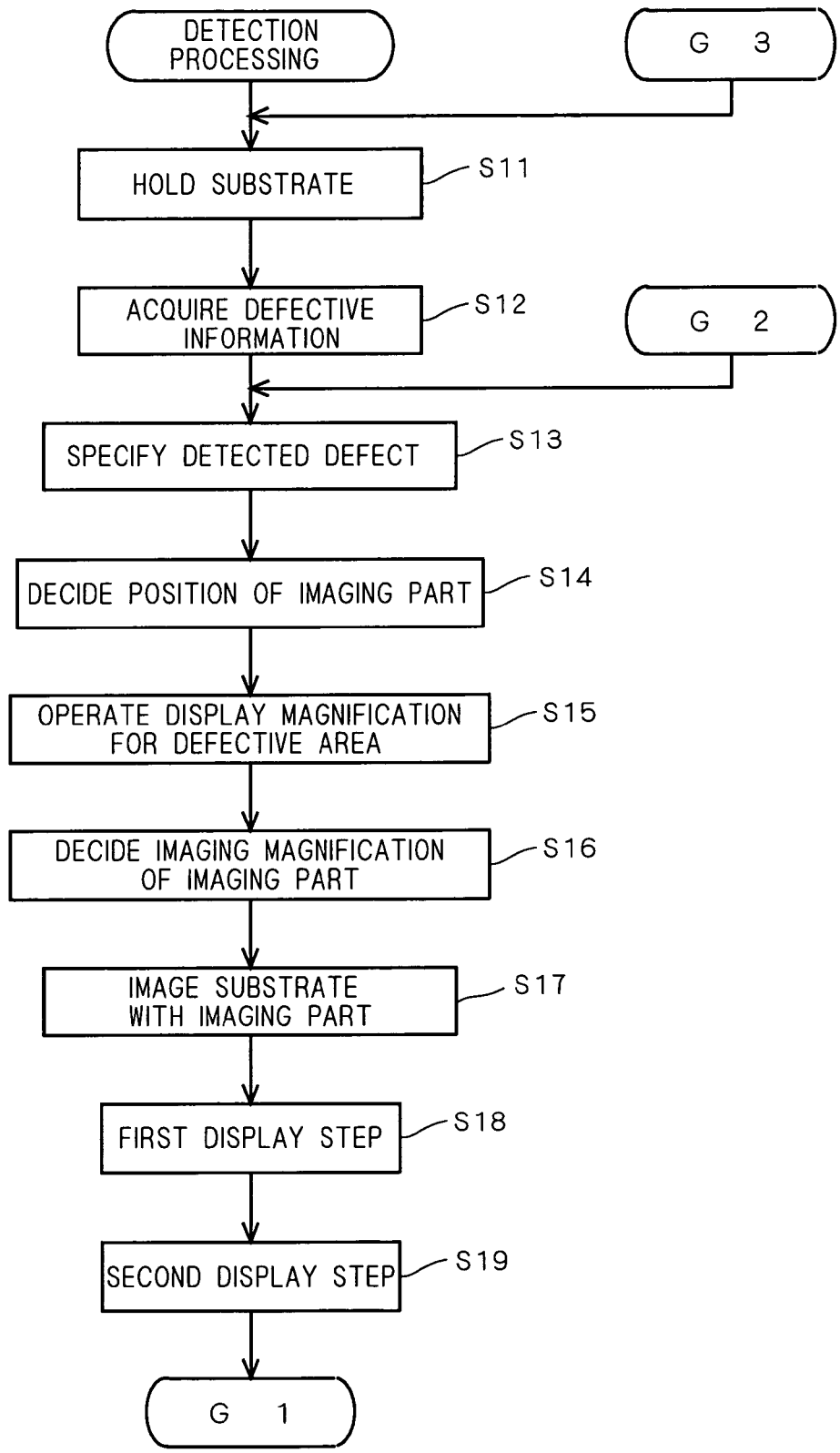
FIGS. 7 and 8 are flow charts showing operations of the defect detector according to the first preferred embodiment.
Figure 8:
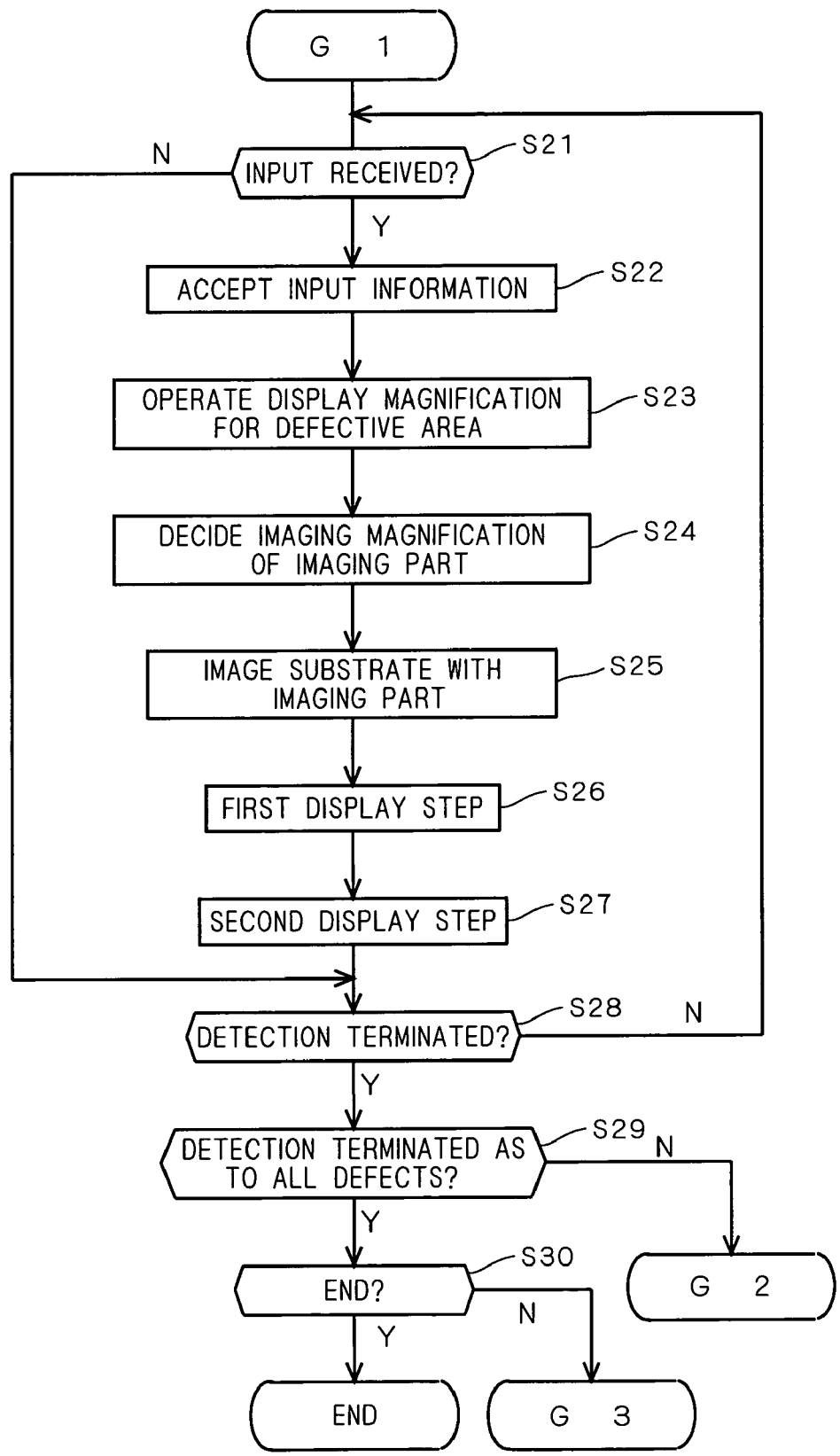

FIGS. 7 and 8 are flow charts showing operations of the defect detector 4 in the defect detection system 1. In the defect detection system 1, the inspection apparatus 3 extracts the defective area of the substrate 90 and creates the defective information 400 in advance of the operations of the defect detector 4.

A transfer apparatus (not shown) or the operator transfers the substrate 90 to be inspected to the defect detector 4, so that the inspection stage 43 thereof holds the substrate 90 on the prescribed position (step S11). The inspection apparatus 3 transmits the defective information 400 for the substrate 90, and the defect detector 4 acquires this defective information 400 through the communication part 47 (step S12).

Then, the control part 48 specifies the detected defect (defective area) of the substrate 90 (step S13). While the control part 48 specifies the defect in order stored in the defective information 400 in the first preferred embodiment, the operator may alternatively select the order.

When the control part 48 specifies the defective area to be detected, the defect detector 4 decides the position of the imaging part 42 (step S14). At the step S14, the defective position-size operation part 481 generates the positional data 402 as to the defective area with reference to the defective information 400. Then, the X/Y control part 483 operates the relative positions of the substrate 90 and the imaging part 42 on the basis of the positional data 402 and obtains the distance for moving the imaging part 42. The X/Y control part 483 further controls the moving mechanisms 44 and 45 thereby moving the imaging part 42 by the obtained distance. Thus, the defect detector 4 decides the position of the imaging part 42.

When the defect detector 4 decides the position of the imaging part 42, the magnification operation part 482 operates the display magnification for the defective area (step S15). At the step S15, the defective position-size operation part 481 transfers the size (Xf, Yf) of the specified defective area with reference to the defective information 400. The defective position-size operation part 481 further transfers the defective area display size (Xw, Yw) to the magnification operation part 482 with reference to the display size data 401. Then, the magnification operation part 482 operates the display magnification α1 for the defective area on the basis of the size of the defective area and the defective area display size.

When the magnification operation part 482 operates the display magnification α1 for the defective area, the magnifications in the X and Y directions must be identical to each other. Further, it is preferable to make a display to include the overall defective area, so that the operator detects the defective area at once. When displaying the defective area, therefore, it is preferable not to excessively enlarge the image data (inspected image data 404) obtained by imaging the defective area. At the step S15, therefore, the magnification operation part 482 obtains the display magnification α1 for the defective area according to the following numerical expression (1):

$$\alpha1 = \min(Xw/Xf, Yw/Yf) \tag{1}$$

where min(A, B) represents the smaller one of values A and B. The defect detector 4 is previously supplied with the initial value of the defective area display size (Xw, Yw) as a size allowing the operator to readily visually recognize the defective area.

Thus, the defect detector 4 setting the initial value of the defective area display size (Xw, Yw) can automatically operate the display magnification α1 for the defective area. Also when the operator inputs no instruction, therefore, the defect detector 4 can display the defective area while enlarging the same to a proper size regardless of the size (Xf, Yf) thereof.

When the magnification operation part 482 obtains the display magnification α1 for the defective area, the defective position-size operation part 481 generates the display magnification data 403 on the basis of the display magnification α1 for the defective area obtained by the magnification operation part 482.

Then, the zoom control part 484 and the zoom mechanism 46 decide the imaging magnification β1 of the imaging part 42 (step S16). A display magnification α for an object is approximated according to the following numerical expression (2) through an imaging magnification β and an enlargement ratio γ by image processing:

$$\alpha = \beta \times \gamma \qquad (2)$$

At the step S16, the zoom control part 484 operates the imaging magnification β1 of the imaging part 42 according to the following numerical expression (3) in response to the display magnification α1 for the defective area with reference to the display magnification data 403:

$$\beta 1 = \alpha 1 \qquad (3)$$

According to the first preferred embodiment, the zoom control part 484 sets the display magnification α1 for the defective area to the imaging magnification β1 of the imaging part 42. This means that the enlargement ratio γ is equal to 1 in the above numerical expression (2). Thus, the defect detector 4 can display the defective area at the previously obtained desired display magnification α1 without performing magnification conversion by image processing on the image data (inspected image data 404) obtained by the imaging part 42.

Then, the zoom control part 484 generates a control signal on the basis of the obtained imaging magnification β1 and controls the zoom mechanism 46. Thus, the zoom mechanism 46 drives the optical system of the imaging part 42 and changes the imaging magnification of the imaging part 42 to the imaging magnification β1.

When the zoom control part 484 and the zoom mechanism 46 decide the imaging position and the imaging magnification β1 of the imaging part 42, the defect detector 4 images the substrate 90 with the imaging part 42 (step S17). At this time, the control part 48 generates a shutter signal for the imaging part 42 and outputs the same to the imaging part 42. The imaging part 42 transmits the acquired image data to the control part 48 as the inspected image data 404, which in turn is stored in the storage part 480. The inspected image data 404 may be a still image or a motion image, or a monochromatic image or a color image. In other words, the inspected image data 404 may be any image so far as the operator can detect the defect in the circuit pattern thereof.

Figure 9:
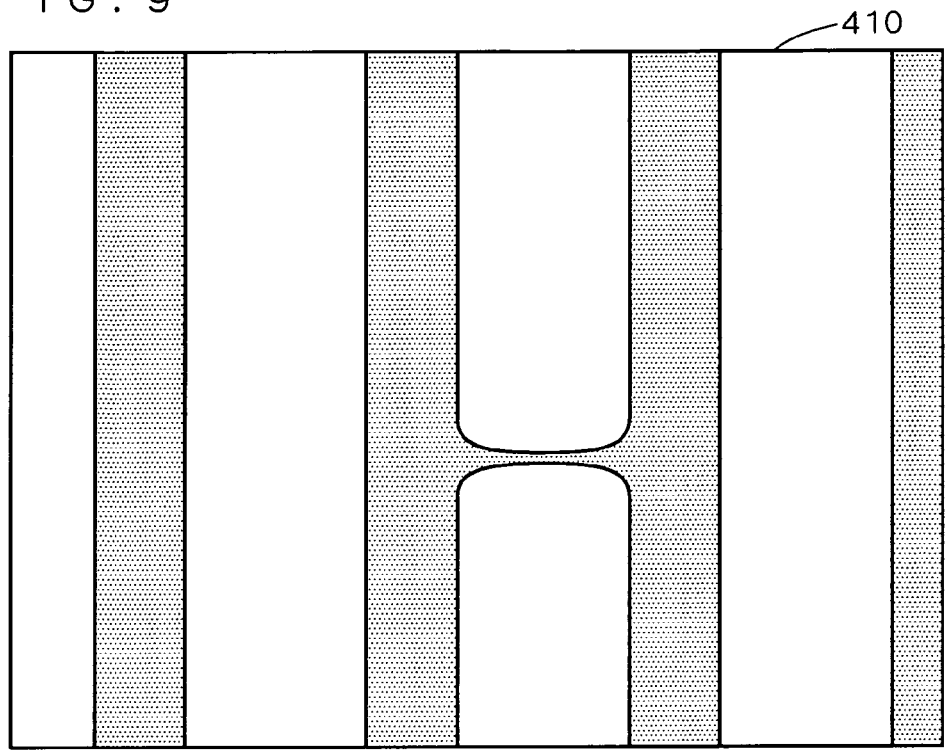
FIGS. 9 and 10 illustrate exemplary displays of inspected image data.
Figure 10:
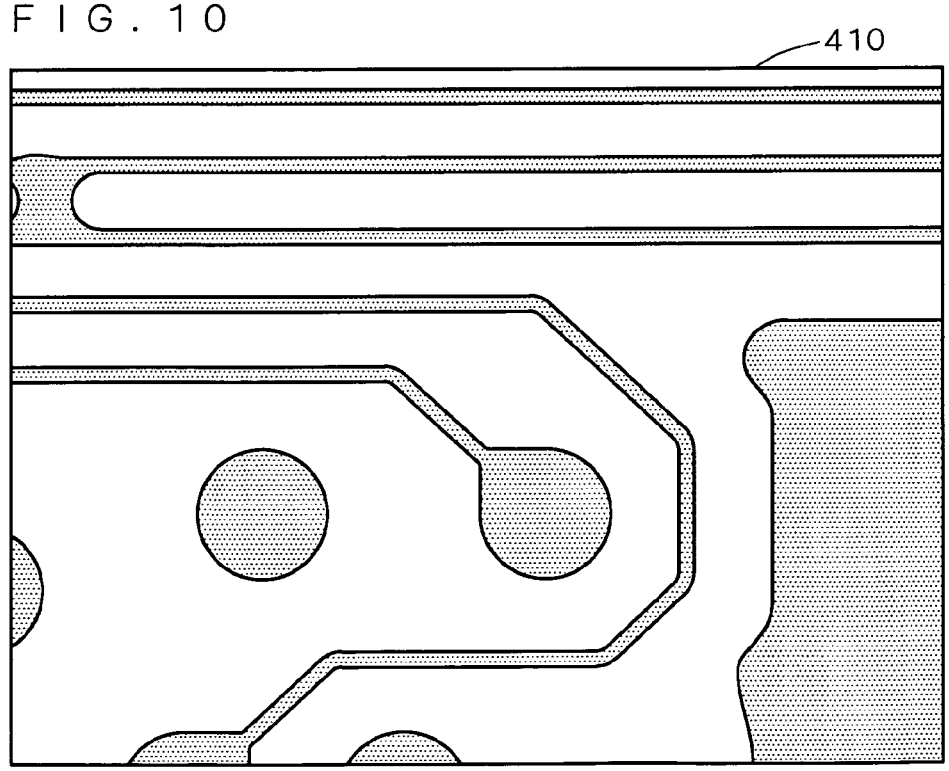

When the imaging part 42 generates the inspected image data 404, the inspected image display part 485 carries out a first display step (step S18). FIGS. 9 and 10 illustrate examples of the inspected image data 404 displayed in the first display step. In the first display step, the inspected image display part 485 displays the inspected image data 404 on the display area 410 of the detection monitor 41 at the display magnification α1 obtained at the step S15. In the defect detector 4 according to the first preferred embodiment, an imaging area of the imaging part 42 is assumed to be substantially identical to the display area 410. The size of the display area 410 (and the size of the imaging area) is rendered larger than the defect display size (Xw, Yw).

As hereinabove described, the defect detector 4 according to the first preferred embodiment obtains the imaging magnification for the inspected image data 404 (imaging magnification β1 of the imaging part 42) according to the numerical expression (3) on the basis of the display magnification α1 for the defective area. Therefore, the operation of the inspected image display part 485 displaying the inspected image data 404 on the display area 410 of the detection monitor 41 substantially at the magnification as such without executing magnification conversion corresponds to an operation of the inspected image display part 485 displaying the inspected image data 404 on the detection monitor 41 in response to the display magnification α1 for the defective area obtained by the magnification operation part 482. In other words, the inspected image display part 485 mainly corresponds to the first display control element in the present invention.

Thus, the defect detector 4 previously imaging the inspected image data 404 at the imaging magnification β1 identical to the display magnification α1 can display the inspected image data 404 without performing magnification conversion (digital zoom processing, for example) by image processing or the like. Therefore, the defect detector 4 can suppress the quantity of operation of the control part 48 in the first display step. If the imaging magnification for the inspected image data 404 is different from the display magnification α1 for the defective area, the inspected image display part 485 may execute magnification conversion processing by image processing on the inspected image data 404 with reference to the display magnification data 403 for displaying the same on the detection monitor 41. In this case, the defect detector 4 can display the inspected image data 404 at a magnification not provided in the zoom mechanism 46.

In a step of manufacturing the substrate 90, various sizes of defective areas of the circuit pattern are formed on the substrate 90. However, the defect detector 4 operates and displays the display magnification for the defective area in response to the size thereof detected by the inspection apparatus 3. Therefore, the defect detector 4 can display the defective area on the detection monitor 41 with the size (Xw, Yw) allowing the operator to readily visually detect the same as shown in FIGS. 9 and 10, regardless of the size of the defective area.

Figure 11:
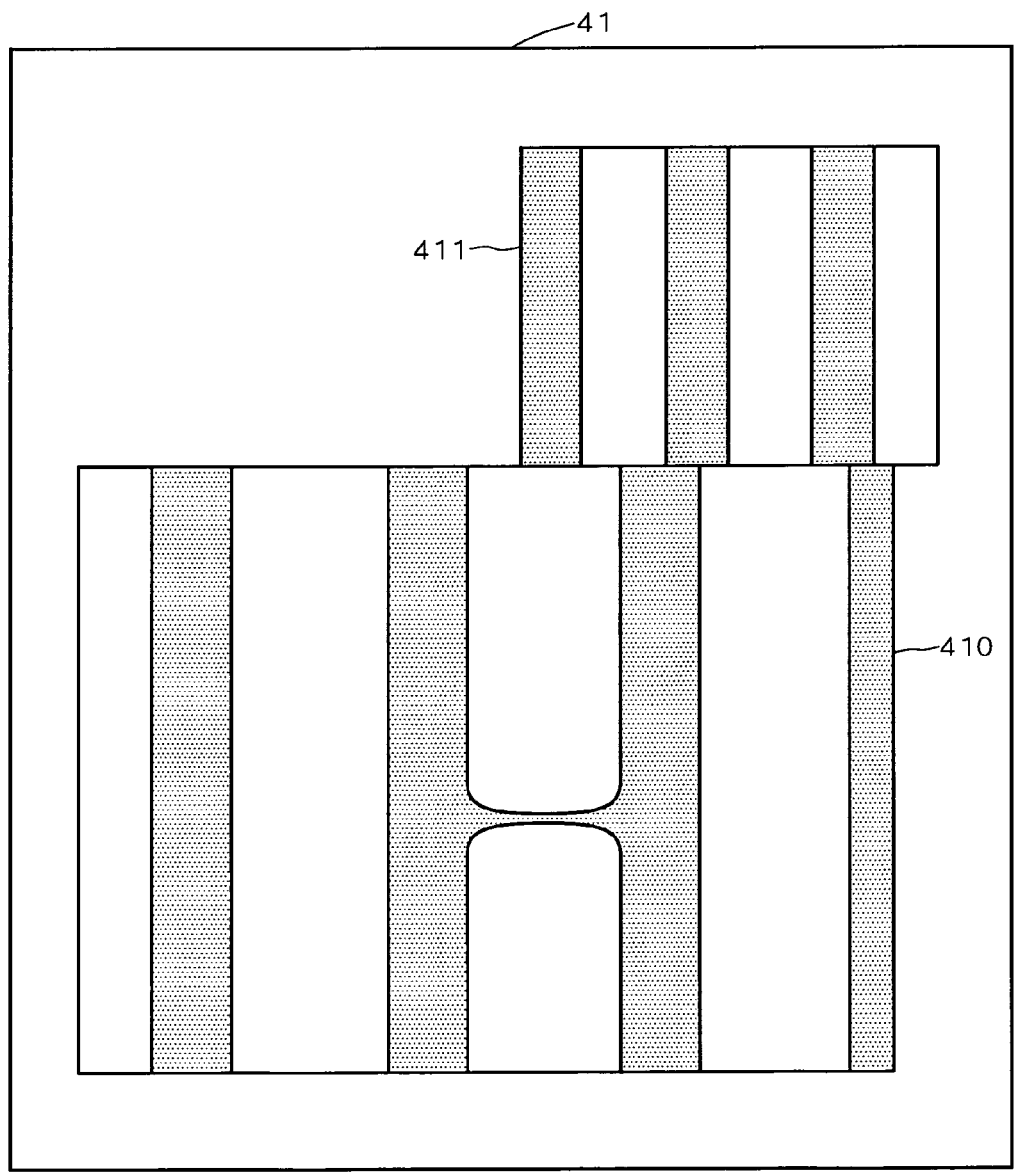

Then, the master image display part 486 carries out a second display step (step S19). In the second display step, the master image display part 486 displays the master image data 405 on the detection monitor 41 at the display magnification α1 obtained at the step S15 with reference to the display magnification data 403. FIGS. 11 and 12 illustrate exemplary screens displayed on the detection monitor 41 through the first and second display steps.

The master image display part 486 obtains the enlargement ratio γ1 for displaying the image data obtained at the imaging magnification β2 with the display magnification α1 according to the following numerical expression (4). Thus, the master image display part 486 determines whether to contractedly or enlargedly display the master image data 405. The numerical expression (4) corresponds to an numerical expression obtained by substituting the display magnification α1 and the imaging magnification β2 in the numerical expression (2) and transferring the items.

$$\gamma 1 = \alpha 1 / \beta 1 \qquad (4)$$

If the enlargement ratio γ1 is less than 1 in the numerical expression (4), this means that the master image data 405 is to be contracted. If the enlargement ratio γ1 is greater or equal to 1, on the other hand, this means that the master image data 405 is enlarged.

In response to the value of the enlargement ratio γ1, therefore, the master image display part 486 obtains the enlargement ratio γ2 for the master image data 405 according to the following numerical expression (5) or (6):

$$\gamma 2 = \gamma 1 \text{ (if } \gamma 1 < 1) \tag{5}$$

$$\gamma 2 = \text{Integer}(\gamma 1) \text{ (if } \gamma 1 \geq 1) \tag{6}$$

where Integer(N) represents an integer part of N. When the master image data 405 is enlarged, therefore, the enlargement ratio γ2 is an integer (natural number) from the numerical expression (6).

When obtaining the enlargement ratio γ2 for the master image data 405, the master image display part 486 obtains the display magnification α2 for the master image data 405 by substituting the same in the numerical expression (2) (numerical expression (7)), performs necessary image processing on the master image data 405 and displays the same on a display area 411 of the detection monitor 41.

$$\alpha 2 = \beta 2 \times \gamma 2 \tag{7}$$

As shown in FIGS. 11 and 12, the screen of the detection monitor 41 is provided with the display area 411 as an area for displaying the master image data 405 along with the display area 410, for simultaneously displaying the inspected image data 404 and the master image data 405. The display magnifications α1 and α2 for the inspected image data 404 and the master image data 405 are rendered substantially identical to each other, so that the detection monitor 41 displays circuit patterns indicated by the image data 404 and 405 substantially at identical sizes.

Figure 21:
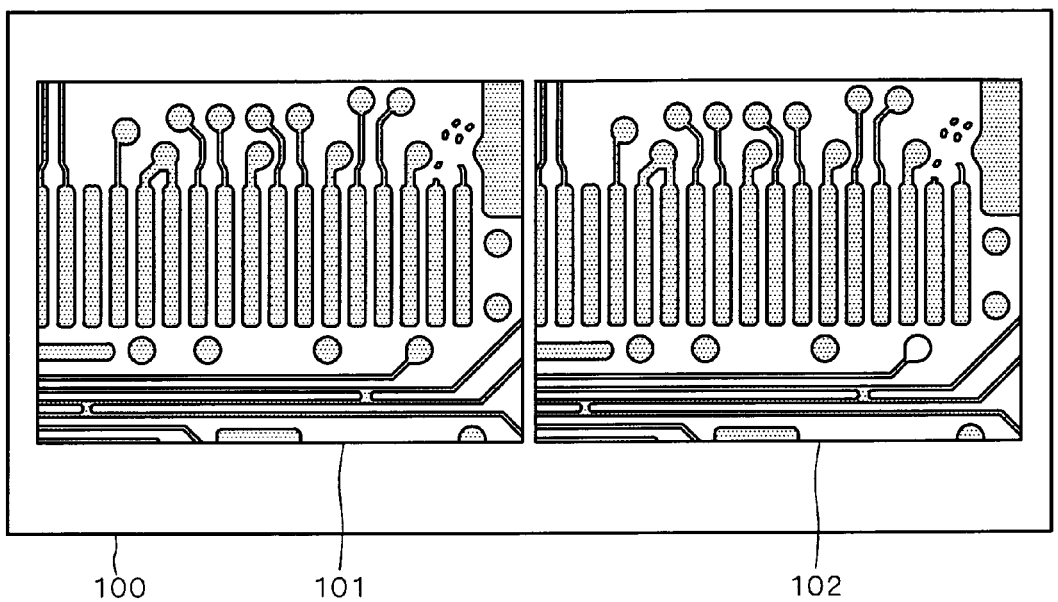
FIGS. 21 illustrate an exemplary display of a master image and an inspected image in a conventional defect detector.
Figure 22:
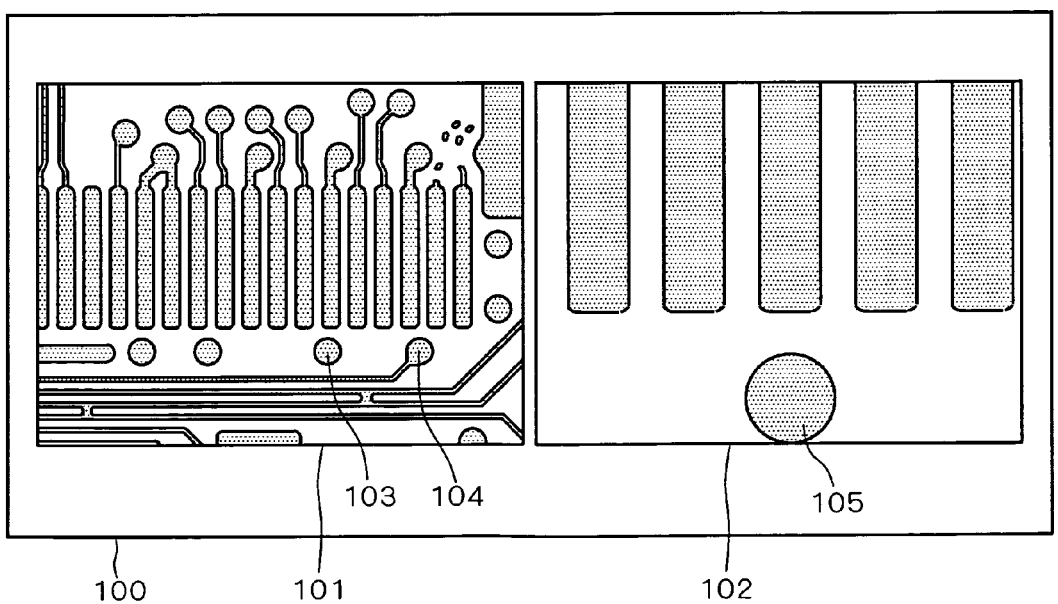
FIG. 22 illustrates exemplary change of a display magnification for the inspected image shown in FIG. 21 in the conventional defect detector.

As shown in FIG. 21, the conventional defect detector is also constituted to display the inspected image and the master image at substantially identical display magnifications on the initial screen (screen displaying the inspected image and the master image in a state not yet changed by the operator). However, the conventional defect detector previously sets the initial values of the imaging magnification for the inspected image and the enlargement ratios for the inspected image and the master image respectively, in order to display the initial screen. Therefore, the conventional defect detector cannot display the inspected image and the master image at the same display magnification even on the initial screen unless the master image has been obtained at a prescribed imaging magnification.

However, the defect detector 4 according to the first preferred embodiment decides the display magnification α1 for the inspected image data 404 for displaying the defective area in a readily detectable size while automatically deciding the display magnification α2 for the master image data 405 following the display magnification α1. Thus, the defect detector 4 can automatically display the master image data 405 previously obtained at an arbitrary imaging magnification at a display magnification substantially equal to that for the inspected image data 404. Therefore, the operator can readily compare a defect reference area and the defective area with each other without finely manually changing the display magnification α2 for the master image data 405. In other words, the defect detector 4 can render the detective operation of the operator efficient. While the display area 410 is larger in size than the display area 411 in the defect detector 4 according to the first preferred embodiment, the display areas 410 and 411 may alternatively display images in the same size, as a matter of course.

When the master image data 405 is digital bit-mapped image data, the defect detector 4 can more correctly display the same at an enlargement magnification multiplied by an integer, without performing interpolation processing between pixels or the like on the master image data 405.

The defect detector 4 according to the first preferred embodiment obtains the enlargement ratio γ2 through the numerical expression (6) for enlarging the master image data 405. However, the method of obtaining the enlargement ratio γ2 to be an integer is not restricted to this. For example, the defect detector 4 may alternatively obtain the enlargement ratio γ2 by rounding off the enlargement ratio γ1 to the first decimal place. When the master image data 405 is analog data or the defect detector 4 performs interpolation processing, the defect detector 4 may obtain the enlargement ratio γ2 through the numerical expression (5) regardless of the value of the enlargement ratio γ1.

When terminating the second display step (step S19), the defect detector 4 monitors whether or not the operator has operated the operation part 40 for inputting an instruction for changing the display magnification α1 (step S21) and waits up to termination of the detective operation as to the defective area (step S28).

If the operator inputs an instruction for changing the display magnification α1 during the detective operation as to the defective area (YES at the step S21), the defect detector 4 accepts the input information from the operation part 40 (step S22) and obtains a new display magnification α1 for the defective area (step S23) for rewriting the display magnification data 403. The term "input information" denotes a changed magnification αp desired by the operator with respect to the currently displayed inspected image data 404. In other words, the defect detector 4 obtains the new display magnification α1 for the defective area through the display magnification αo for the defective area theretofore displayed according to the following numerical expression (8):

$$\alpha 1 = \alpha p \times \alpha o \tag{8}$$

In other words, the defect detector 4 rewrites the display magnification α1 for the defective area indicated by the display magnification data 403 to the value obtained through the numerical expression (8) at the step S23.

Then, the zoom control part 484 operates a new imaging magnification β1 of the imaging part 42 on the basis of the display magnification data 403 rewritten at the step S23 and controls the zoom mechanism 46 thereby newly deciding the imaging magnification of the imaging part 42 (step S24).

When the zoom control part 484 decides the imaging magnification, the imaging part 42 images the substrate 90 (step S25) for newly acquiring inspected image data 404. Further, the inspected image display part 485 carries out the first display step (step S26) for displaying the new inspected image data 404 on the display area 410 of the detection monitor 41.

At this time, the inspected image display part 485 displays the inspected image data 404 imaged at the new display magnification α1 desired by the operator as such, similarly to the step S18. Thus, the defect detector 4 displays the defective area specified at the step S13 at the new display magnification α1 desired by the operator.

When the inspected image display part 485 displays the inspected image data 404, the master image display part 486 carries out the second display step (step S27) for displaying the master image data 405. At this time, the defect detector 4 operates the display magnification α2 for the master image data 405 by a method similar to that employed at the step S19 on the basis of the display magnification data 403 rewritten at the step S23.

Figure 13:
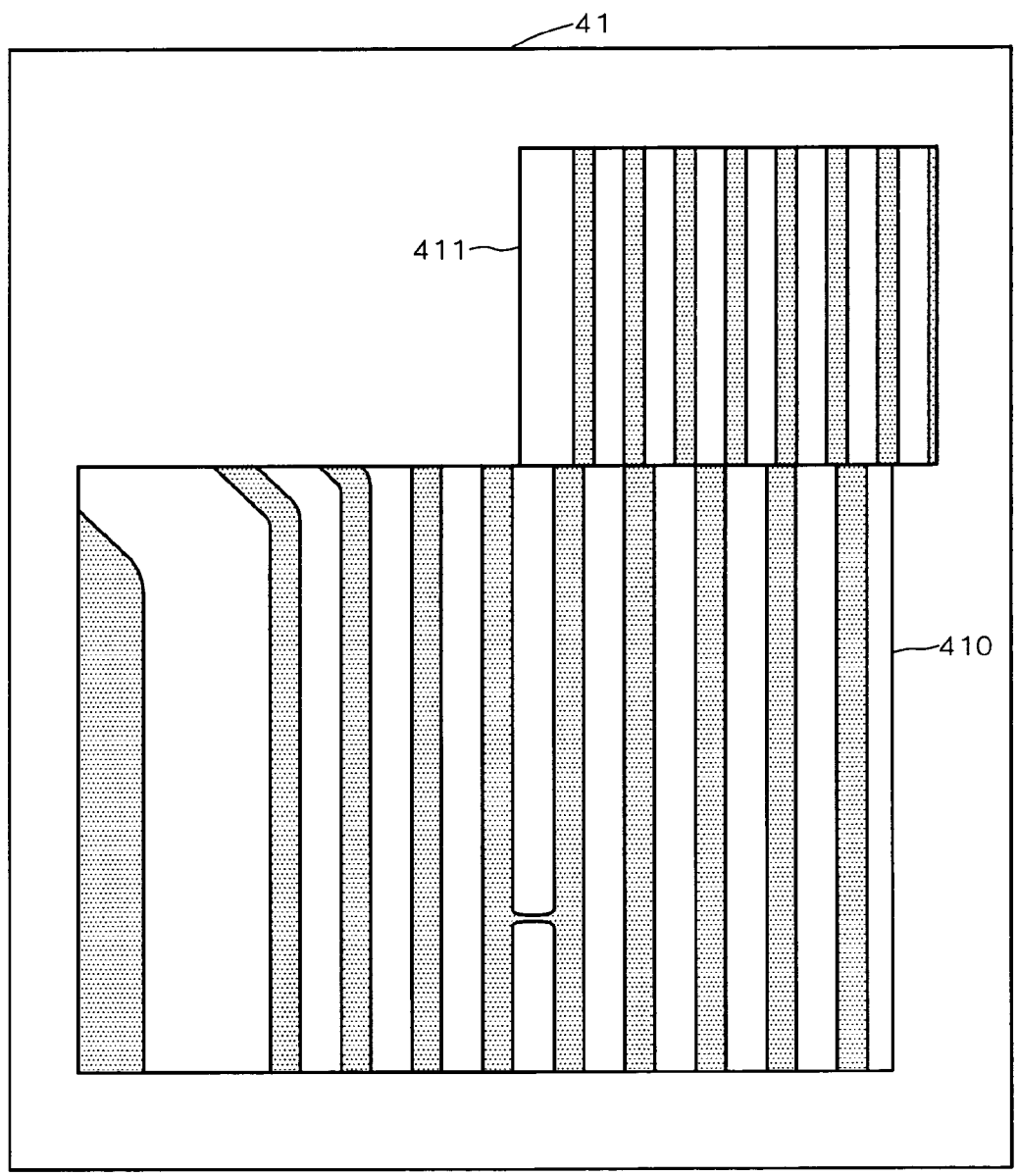
FIG. 13 illustrates exemplary change of a display magnification for inspected image data with reference to FIG. 11.

FIG. 13 illustrates exemplary change of the display magnification α1 for the inspected image data 404 as to the example shown in FIG. 11. When changing the inspected image data 404 displayed on the display area 410 shown in FIG. 11 to the inspected image data 404 displayed on the display area 410 shown in FIG. 13, the defect detector 4 displays the master image data 405 on the display area 411 shown in FIG. 13 at a display magnification substantially identical to the changed display magnification α1 for the inspected image data 404.

In other words, the defect detector 4 automatically displays the master image data 405 at the display magnification α2 following the display magnification α1 for the inspected image data 404 when the operator changes the display magnification α1 for the inspected image data 404. Therefore, the operator can readily compare the image data 404 and 405 with each other without performing an operation of changing the display magnification α2 for the master image data 405 for improving the efficiency of the detective operation.

Referring again to FIG. 8, the control part 48 refers to the defective information 400 when the operator terminates the detective operation with respect to the defective area (YES at the step S28) for confirming whether or not the operator has terminated the detective operation as to all defective areas of the substrate 90, and repeats the processing from the step S13 when another defective area is present.

If no other defective area to be detected is present (YES at the step S29), the control part 48 determines whether or not there is another substrate to be inspected (step S30). The control part 48 repeats the processing from the step S11 if there is another substrate to be inspected, while terminating the processing if there is no other substrate to be inspected.

As hereinabove described, the defect detector 4 according to the first preferred embodiment operates the display magnification α2 for the master image data 405 to be compared with the defective area on the basis of the display magnification α1 for the defective area obtained by the magnification operation part 482. The defect detector 4 displays the master image data 405 on the detection monitor 41 in response to the obtained display magnification α2, so that the same can display the master image data 405 imaged at an arbitrary imaging magnification in response to the display magnification α1 for the inspected image data 404. Therefore, the operator can readily compare the image data 404 and 405 with each other for improving the efficiency of the defect detective operation.

When the operator changes the display magnification α1 for the inspected image data 404, the defect detector 4 also automatically changes the display magnification α2 for the master image data 405, whereby the operator can perform the detective operation without finely changing the display magnification α2 for the master image data 405 dissimilarly to the conventional defect detector. The efficiency of the defect detective operation can be improved also by this.

Further, the defect detector 4 simultaneously displays the inspected image data 404 and the master image data 405 on the detection monitor 41, whereby the operator can readily compare the defective area and the defect reference area with each other.

When the operator directly drives the optical system of the imaging part 42 (directly changes the imaging magnification β1), the defect detector 4 reads the imaging magnification β1 of the imaging part 42 through the position of the driven optical system of the imaging part 42 and regards this imaging magnification β1 as the display magnification α1 through the numerical expression (3). In other words, the defect detector 4 may receive the display magnification α1 through this operation. In this case, the zoom control part 484 may not control the zoom mechanism 46, whereby the defect detector 4 may not newly obtain the imaging magnification β1 on the basis of the received display magnification α1.

While the defect detector 4 according to the first preferred embodiment simultaneously displays the master image data 405 and the inspected image data 404, the method of displaying the image data 404 and 405 is not restricted to this but the defect detector 4 may alternatively display the image data 404 and 405 in a switching manner.

Figure 14:
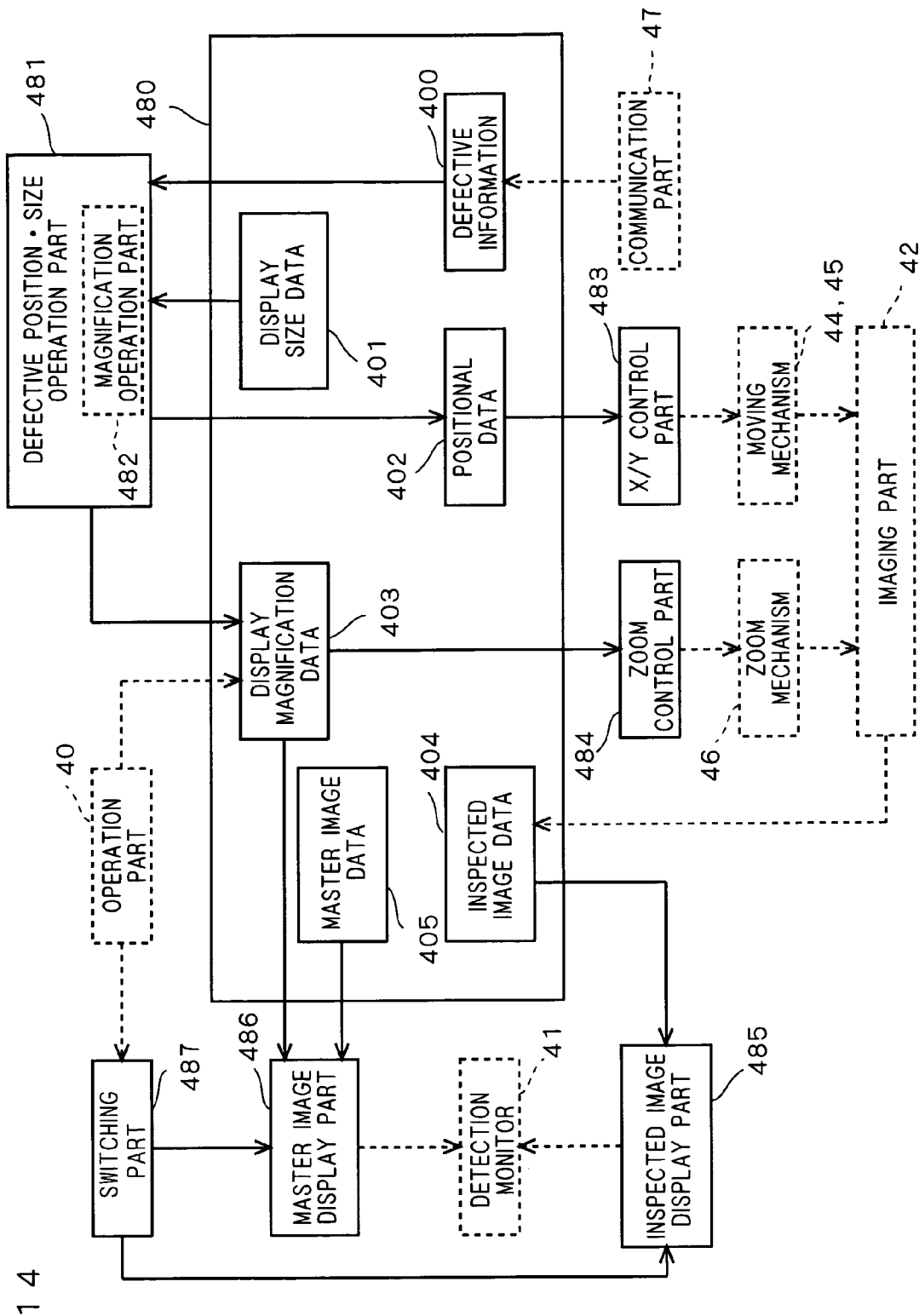
FIG. 14 is a block diagram showing the functional structure of a control part of a defect detector according to a second preferred embodiment along with data flows.

FIG. 14 is a block diagram showing the functional structure of a control part 48 of a defect detector 4 according to a second preferred embodiment of the present invention structured on the basis of the aforementioned principle along with data flows. The defect detector 4 according to the second preferred embodiment is different from the defect detector 4 according to the first preferred embodiment in a point that the same comprises a switching part 487 in the functional structure of the control part 48. Structures of the defect detector 4 according to the second preferred embodiment having functions similar to those of the defect detector 4 according to the first preferred embodiment are denoted by the same reference numerals, for properly omitting redundant description.

The switching part 487 accepts an input signal from an operation part 40 for switching displays of inspected image data 404 and master image data 405 on an inspected image display part 485 and a master image display part 486 on the basis of the input signal.

Figure 15:
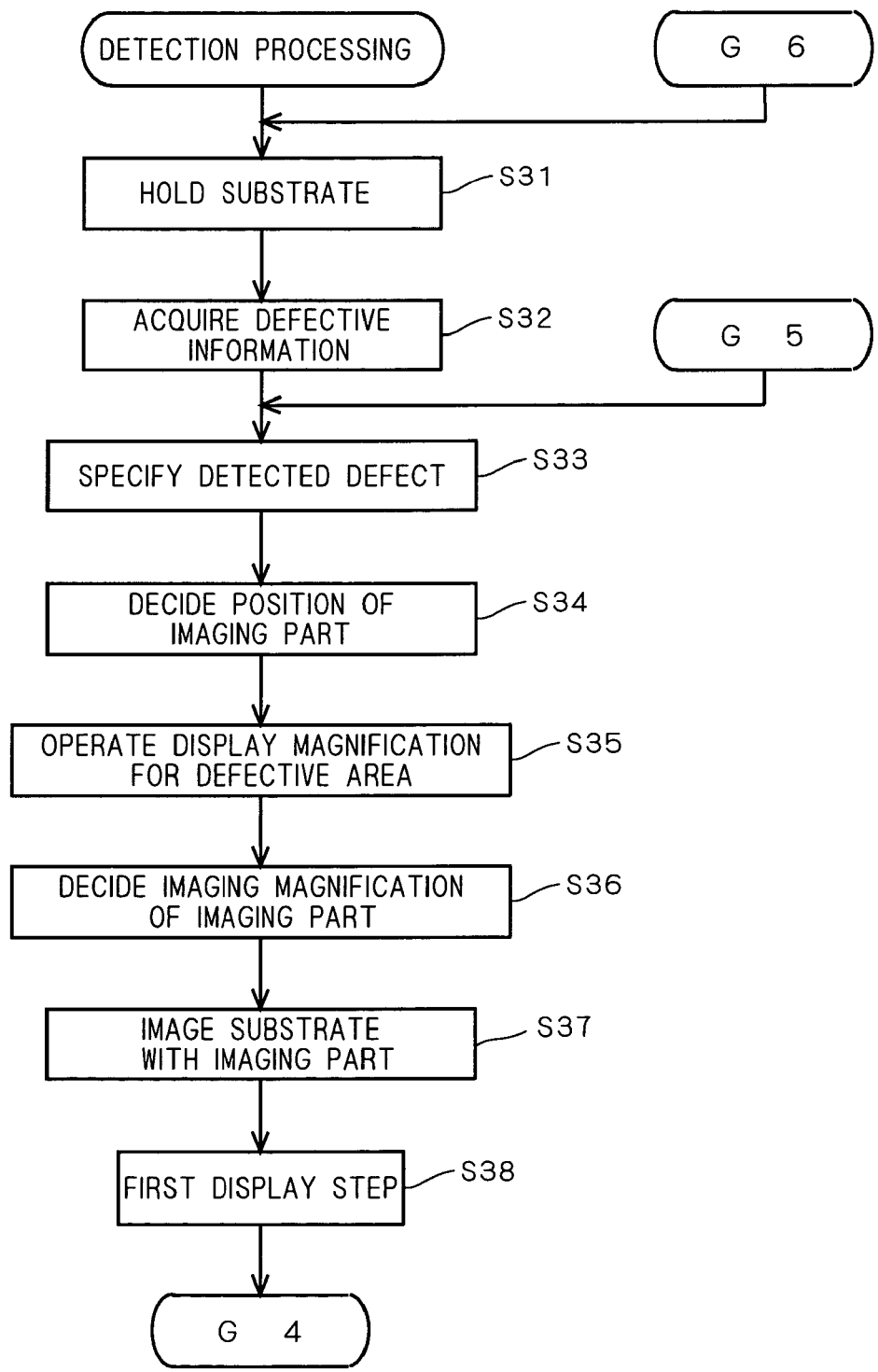

FIGS. 15 and 16 are flow charts showing operations of the defect detector 4 according to the second preferred embodiment. Steps S31 to S37 shown in FIG. 15 are similar to the steps S11 to S17 shown in FIG. 7.

The defect detector 4 carries out a step S38 for displaying the inspected image data 404 on a detection monitor 41 similarly to the step S18 shown in FIG. 7, without carrying out processing corresponding to the step S19. This is because the defect detector 4 according to the second preferred embodiment is set to display the inspected image data 404 on the inspected image display part 485 in the initial state and the switching part 487 lets the inspected image display part 485 display the inspected image data 404 when receiving no instruction from an operator.

Thus, the operator can recognize that an imaging part 42 has imaged a substrate 90 and start visually detecting a defective area.

Figure 17:
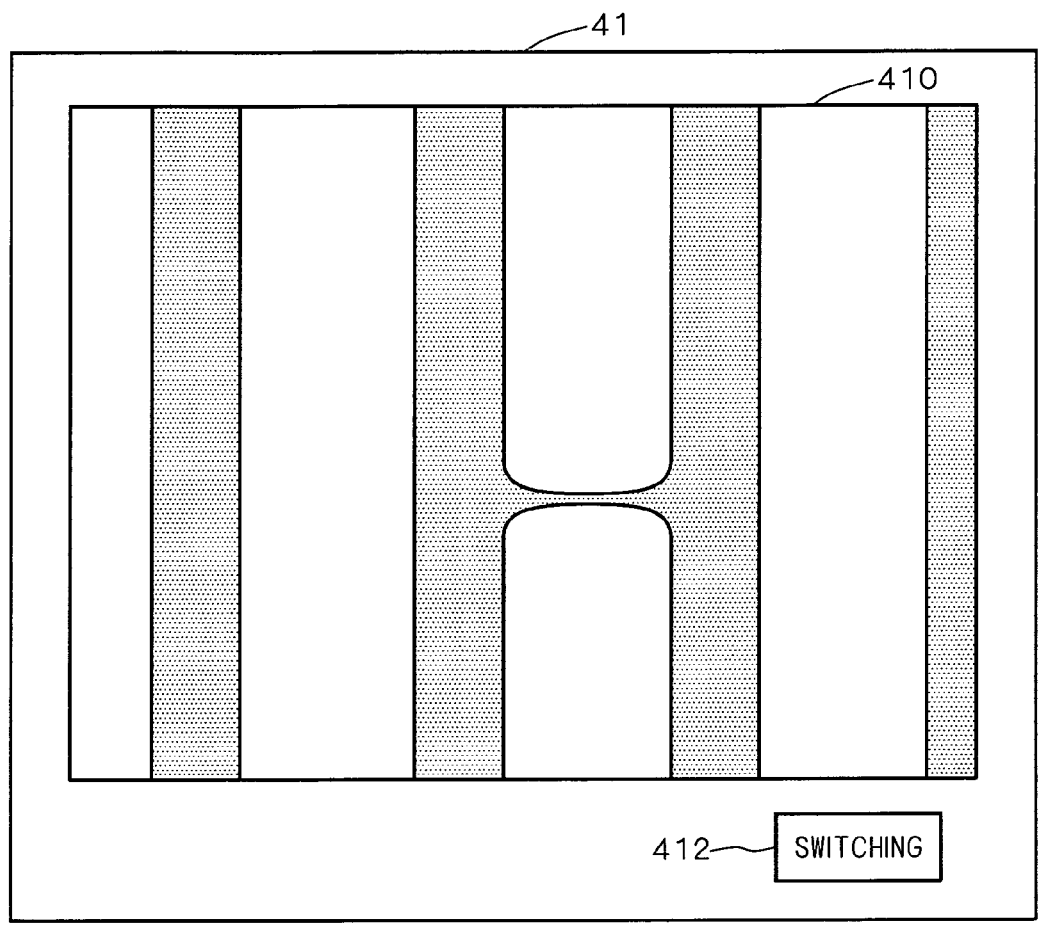
FIG. 17 illustrates an exemplary display of inspected image data in the defect detector according to the second preferred embodiment.

FIG. 17 illustrates an exemplary display made on the detection monitor 41 in the aforementioned manner. As shown in FIG. 17, the display screen of the detection monitor 41 is assigned only to a switching button 412 and a display area 410, for displaying only the inspected image data 404. The function of the switching button 412 is described later.

When the detection monitor 41 displays the inspected image data 404, the defect detector 4 according to the second preferred embodiment determines whether or not the operator has made an input (step S41). This determination processing corresponds to the step S21.

The defect detector 4 executes processing through steps S42 to S45 (corresponding to the processing through the steps S22 to S25 shown in FIG. 8) if the determination at the step S41 is of YES, while skipping this processing if the determination is of NO.

Then, the switching part 487 determines whether or not the operator has operated the switching button 412 with reference to an input signal from the operation part 40, thereby determining whether or not to display a defect reference area (step S46). In other words, the switching button 412 has a function of inputting an instruction from the operator in the switching part 487.

If the operator has not operated the switching button 412 (NO at the step S46), the switching part 487 carries out a first display step at a step S47 (corresponding to the processing at the step S26) in order to make a display on the inspected image display part 485. If the defect detector 4 has already executed the processing at the steps S42 to S45, the switching part 487 operates and displays a display magnification $\alpha 1$ for the inspected image data 404 again.

If the operator has operated the switching button 412 (YES at the step S46), on the other hand, the switching part 487 carries out a second display step at a step S48 (corresponding to the processing at the step S27) in order to make a display on the master image display part 486.

FIG. 18 illustrates an exemplary display made on the detection monitor 41 in the aforementioned manner. As shown in FIG. 18, the switching part 487 switches the display through the inspected image display part 485 to the display through the master image display part 486, and the display screen of the detection monitor 41 is assigned to only a return button 413 and a display area 411. The return button 413 is employed for returning the display to that through the inspected image display part 485. In other words, the defect detector 4 makes a determination of YES at the step S46 unless the return button 413 is operated.

Processing through steps S49 to S51 executed following the step S47 or S48 is similar to the processing through the steps S28 to S30 shown in FIG. 8.

As hereinabove described, the defect detector 4 according to the second preferred embodiment can also attain effects similar to those of the defect detector 4 according to the first preferred embodiment.

Further, the defect detector 4 can effectively utilize the display area of the detection monitor 41 by switching the display between that through the inspected image display part 485 and that through the master image display part 486.

While each of the first and second preferred embodiments has been described with reference to the defect detector 4 displaying the master image data 405 and the inspected image data 404 on the single detection monitor 41, the method of displaying the image data 404 and 405 is not restricted to this but the image data 404 and 405 may alternatively be displayed on different displays respectively.

Figure 19:
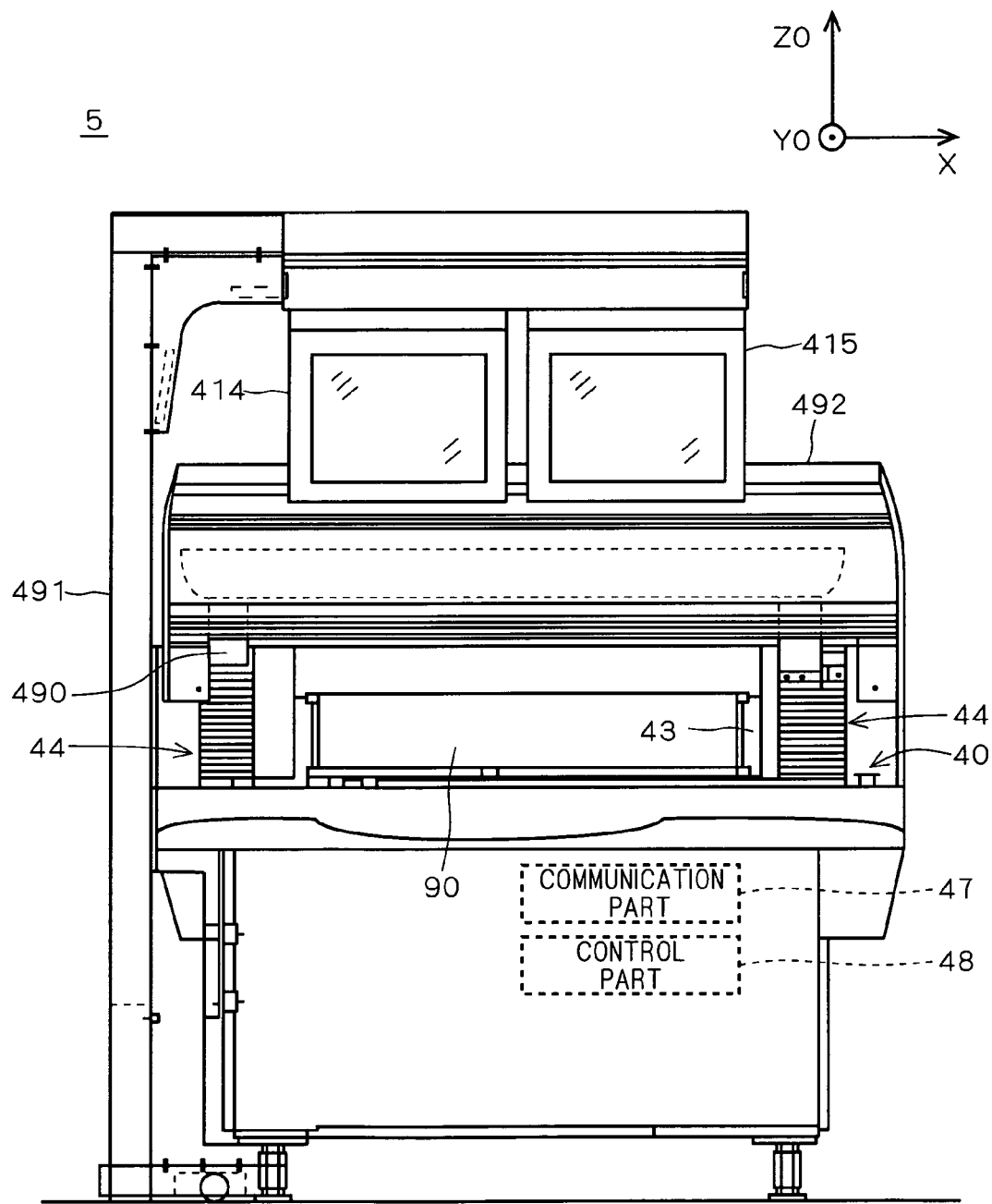
FIG. 19 is a front elevational view of a defect detector according to a third preferred embodiment of the present invention.

FIG. 19 is a front elevational view of a defect detector 5 according to a third preferred embodiment of the present invention structured on the basis of the aforementioned principle. The defect detector 5 according to the third preferred embodiment comprises two detection monitors 414 and 415 as displays displaying various data on screens thereof. The defect detector 5 is substantially similar in structure to the defect detector 4 according to the first preferred embodiment except the detection monitors 414 and 415, and portions of the defect detector 5 according to the third preferred embodiment similar to those of the defect detector 4 according to the first preferred embodiment are properly denoted by the same reference numerals, to omit redundant description.

The detection monitors 414 and 415, having functions similar to that of the detection monitor 41 according to the aforementioned first preferred embodiment respectively, are arranged in an X-axis direction and supported by a support member 491, as shown in FIG. 19.

Figure 20:
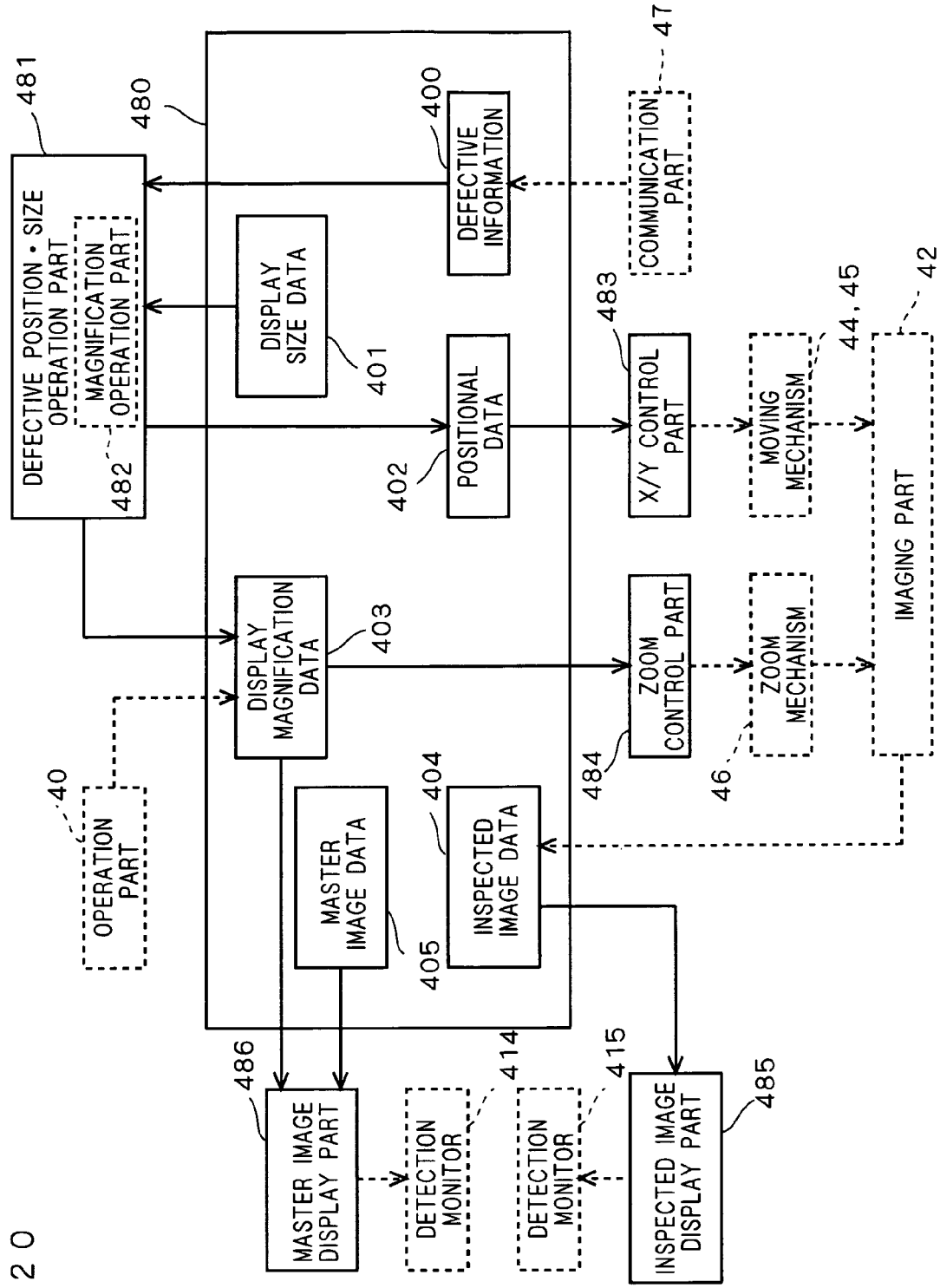
FIG. 20 is a block diagram showing the functional structure of a control part of the defect detector according to the third preferred embodiment along with data flows.

FIG. 20 is a block diagram showing the functional structure of a control part 48 in the defect detector 5 according to the third preferred embodiment along with data flows. In the control part 48 according to the third preferred embodiment, an inspected image display part 485 makes an output to the detection monitor 415, while a master image display part 486 makes an output to the detection monitor 414.

While the defect detector 5 according to the third preferred embodiment is constituted as an apparatus executing operations similar to those of the defect detector 4 according to the first preferred embodiment shown in FIGS. 7 and 8, the inspected image display part 485 displays inspected image data 404 on the detection monitor 415 at steps similar to the steps S18 and S26. Further, the master image display part 486 displays master image data 405 on the detection monitor 414 at steps similar to the steps S19 and S27.

Thus, the defect detector 5 can avoid such a possibility that an operator mistakes the inspected image data 404 for the master image data 405 or vice versa in an operation of detecting a defect by displaying a defective area and a defect reference area on different displays.

As hereinabove described, the defect detector 5 according to the third preferred embodiment can also attain effects similar to those of the defect detector 4 according to the aforementioned first preferred embodiment.

Further, the operator hardly mistakes the inspected image data 404 for the master image data 405 or vice versa in the operation of detecting the defect. Therefore, the defect detector 5 can render the detective operation efficient.

In each of the aforementioned preferred embodiments, the method of acquiring the defective information 400 is not restricted to the operation of the communication part 47 through the network 2. The inspection apparatus 3 may alternatively record the defective information 400 in a portable recording medium or the like for transferring the recording medium to the defect detector 4 or 5 along with the substrate 90 so that the defect detector 4 or 5 reads the defective information 400 from the recording medium.

While the control part 48 implements its functional structure by running a program through software processing in each of the aforementioned preferred embodiments, the control part 48 may alternatively partially or entirely implement its functional structure by hardware processing through a dedicated circuit such as a capture board or an axis control board.

The order of the processing in the defect detector 4 or 5 is not restricted to that described with reference to each of the aforementioned preferred embodiments. For example, the defect detector 4 according to the first preferred embodiment may alternatively be structured to parallelly execute the processing at the step S14 and that at the steps S15 and 16, or switch the order of carrying out the steps S18 and S19. In other words, the defect detector 4 may execute the processing at any order so far as effects similar to the above can be attained.

While the operator inputs the changed magnification $\alpha p$ for the currently displayed inspected image data 404 in order to change the display magnification therefor in each of the aforementioned first to third preferred embodiments, the input information is not restricted to this. For example, the operator may alternatively directly input a new desired display magnification $\alpha 1$. Further alternatively, the operator may input a new defect display size for rewriting the display size data 401 so that the magnification operation part 482 operates a new display magnification $\alpha 1$.

While the defect detector 4 or 5 obtains the master image data 405 by previously imaging a reference substrate and preserves the same or creates the same from CAD data, the operator may alternatively acquire the master image data 405 in real time when detecting the defective area. In this case, the defect detector 4 or 5 may set the imaging magnification $\beta 2$ for the reference substrate following the display magnification $\alpha 1$ for the inspected image data 404.

While the invention has been shown and described in detail, the foregoing description is in all aspects illustrative and not restrictive. It is therefore understood that numerous modifications and variations can be devised without departing from the scope of the invention.

What is claimed is:

1. A defect detector for detecting a defect on an inspected object, comprising:
   an image display system;
   a holding element holding said inspected object;
   an image acquisition element imaging said inspected object held by said holding element for acquiring inspected image data obtained by imaging a defective area of said inspected object having a defect;
   a first display control element configured to display said inspected image data acquired by said image acquisition element on said image display system at a first display magnification; and
   a second display control element configured to display master image data to be compared with said defective area on said image display system at a second display magnification substantially the same as said first display magnification.

2. The defect detector according to claim 1, further comprising:
   a size acquisition element acquiring information indicating the size of said defective area as to said inspected object held by said holding element, and
   a display magnification operational element operating said first display magnification according to a prescribed algorithm on the basis of said information indicating the size of said defective area acquired by said size acquisition element.

3. The defect detector according to claim 1, further comprising an operation part accepting input information from an operator, wherein
   said second display control element operates said second display magnification in response to set said first display magnification every time said first display magnification is set on the basis of said input information and displays said master image data on said image display system at said second display magnification.

4. The defect detector according to claim 1, further comprising an imaging magnification decision element deciding an imaging magnification of said image acquisition element for imaging said inspected object according to a prescribed algorithm in response to said first display magnification.

5. The defect detector according to claim 1, further comprising:
   a position acquisition element acquiring information indicating the position of said defective area as to said inspected object held by said holding element, and
   a positioning element deciding relative positions of said inspected object held by said holding element and said image acquisition element in response to said information indicating the position of said defective area acquired by said position acquisition element.

6. The defect detector according to claim 1, wherein
   said master image data expresses a digital bit-mapped image, and
   said second display magnification is a magnification value for enlarging said digital bit-mapped image to integral times.

7. The defect detector according to claim 1, wherein
   a single display included in said image display system simultaneously displays said inspected image data and said master image data by said first display control element and said second display control element respectively.

8. The defect detector according to claim 1, further comprising a switching element making said single display included in said image display system display said inspected image data and said master image data by said first display control element and said second display control element in a switching manner.

9. The defect detector according to claim 1, wherein
   said image display system comprises:
   a first display displaying said inspected image data under control of said first display control element, and
   a second display displaying said master image data under control of said second display control element.

10. A defect detecting method of defecting a defect on an inspected object, comprising:
    a holding step of holding said inspected object;
    an image acquisition step of imaging said inspected object held in said holding step and acquiring inspected image data obtained by imaging a defective area of said inspected object having a defect;
    a first display step of displaying said inspected image data acquired in said image acquisition step on an image display system at a first display magnification; and
    a second display step of displaying master image data to be compared with said defective area on the image display system at a second display magnification substantially the same as said first display magnification.

11. The defect detection method according to claim 10, further comprising:
    a size acquisition step of acquiring information indicating the size of said defective area as to said inspected object held in said holding step, and
    a display magnification operation step of operating said first display magnification according to a prescribed algorithm on the basis of said information indicating the size of said defective area acquired in said size acquisition step.

12. The defect detection method according to claim 10, further comprising an operation step of accepting input information from an operator,
    for carrying out said second display step every time said first display magnification is set on the basis of said input information.

13. The defect detection method according to claim 10, further comprising an imaging magnification decision step of deciding an imaging magnification for imaging said inspected object according to a prescribed algorithm in response to said first display magnification.

14. The defect detection method according to claim 10, further comprising:
    a position acquisition step of acquiring information indicating the position of said defective area as to said inspected object held in said holding step, and
    a positioning step of deciding relative positions of said inspected object held in said holding step and an imaging element imaging said inspected object in response to said information indicating the position of said defective area acquired in said position acquisition step.

15. The defect detection method according to claim 10, wherein
    said master image data expresses a digital bit-mapped image, and
    said second display magnification is operated as a magnification value for enlarging said digital bit-mapped image to integral times in said second display step.

* * * * *